US009139524B2

(12) United States Patent
Corminboeuf et al.

(10) Patent No.: US 9,139,524 B2
(45) Date of Patent: Sep. 22, 2015

(54) FLUORINATED BRIDGED SPIRO[2.4]HEPTANE DERIVATIVES AS ALX RECEPTOR AGONISTS

(71) Applicant: Actelion Pharmaceuticals Ltd., Allschwil (CH)

(72) Inventors: Olivier Corminboeuf, Allschwil (CH); Davide Pozzi, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 14/401,769

(22) PCT Filed: May 15, 2013

(86) PCT No.: PCT/IB2013/053976
§ 371 (c)(1),
(2) Date: Nov. 17, 2014

(87) PCT Pub. No.: WO2013/171694
PCT Pub. Date: Nov. 21, 2013

(65) Prior Publication Data
US 2015/0118258 A1    Apr. 30, 2015

(30) Foreign Application Priority Data

May 16, 2012  (EP) .................................. 12168322

(51) Int. Cl.
C07D 211/58 (2006.01)
C07D 207/14 (2006.01)
(52) U.S. Cl.
CPC ............ C07D 211/58 (2013.01); C07D 207/14 (2013.01)
(58) Field of Classification Search
None
See application file for complete search history.

(56) References Cited

FOREIGN PATENT DOCUMENTS

| WO | 9502587 | A1 | 1/1995 |
|---|---|---|---|
| WO | 03082314 | A2 | 10/2003 |
| WO | 2005040120 | A1 | 5/2005 |
| WO | 2005047899 | A2 | 5/2005 |
| WO | 2005090330 | A1 | 9/2005 |
| WO | 2006114401 | A2 | 11/2006 |
| WO | 2008121687 | A2 | 10/2008 |
| WO | 2009077954 | A1 | 6/2009 |
| WO | 2009077990 | A1 | 6/2009 |
| WO | 2010134014 | A1 | 11/2010 |
| WO | 2010143116 | A1 | 12/2010 |
| WO | 2010143158 | A1 | 12/2010 |
| WO | 2011163502 | A1 | 12/2011 |
| WO | 2012066488 | A2 | 5/2012 |
| WO | 2012077049 | A1 | 6/2012 |
| WO | 2012077051 | A1 | 6/2012 |
| WO | 2013009543 | A1 | 1/2013 |
| WO | 2013171687 | A1 | 11/2013 |
| WO | 2014138037 | A1 | 9/2014 |
| WO | 2014138046 | A1 | 9/2014 |

OTHER PUBLICATIONS

Bannenberg, Gerard L., "Anti-inflammatory actions of lipoxins," Expert Opinion on Therapeutic Patents, Informa Healthcare, (2007), vol. 17, No. 6, pp. 591-605.
Bürli, Roland W. et al., "Potent hFPRL1 (ALXR) agonists as potential anti-inflammatory agents," Bioorganic & Medicinal Chemistry Letters, (2006), vol. 16, No. 4, pp. 3713-3718.
Celik, G.E. et al., "Lipoxin A4 levels in asthma: relation with disease severity and aspirin sensitivity," Clinical and Experimental Allergy, (2007), vol. 37, pp. 1494-1501.
Chiang, Nan et al., "The Lipoxin Receptor ALX: Potent Ligand-Specific and Stereoselective Actions in Vivo," Pharmacological Reviews, (2006), vol. 58, No. 3, pp. 463-487.
Edwards, Bruce S. et al., "Integration of Virtual Screening with High-Throughput Flow Cytometry to Identify Novel Small Molecule Formylpeptide Receptor Antagonists," Molecular Pharmacology, (2005), vol. 68, No. 5, pp. 1301-1310.
Gewirtz, Andrew T. et al., "Mechanisms of Active Intestinal Inflammation and Potential Down-Regulation Via Lipoxins," Advances in Experimental Medicine and Biology, (2002), vol. 507, pp. 229-236.
Gould, Philip L., "Salt selection for basic drugs," International Journal of Pharmaceutics, (1986), vol. 33, pp. 201-217.
Gronert, Karsten et al., "A Role for the Mouse 12/15-Lipoxygenase Pathway in Promoting Epithelial Wound Healing and Host Defense," The Journal of Biological Chemistry, (2005), vol. 280, No. 15, pp. 15267-15278.
Gronert, Karsten, "Lipoxins in the eye and their role in wound healing," Prostaglandins, Leukotrienes and Essential Fatty Acids, (2005), vol. 73, pp. 221-229.

(Continued)

Primary Examiner — Timothy R Rozof
(74) Attorney, Agent, or Firm — Hunton & Williams LLP

(57) ABSTRACT

The present invention relates to fluorinated bridged spiro[2.4] heptane derivatives of formula (I),

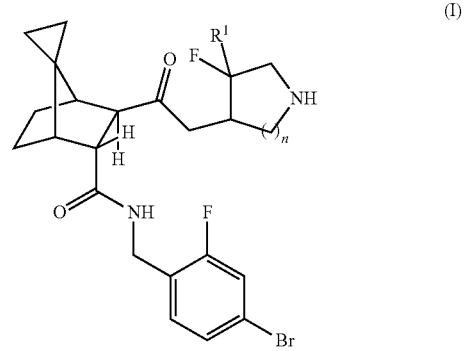

wherein n and $R^1$ are as defined in the description, their preparation and their use as pharmaceutically active compounds.

17 Claims, No Drawings

(56) References Cited

OTHER PUBLICATIONS

Jin, Sheng-Wei et al., "Posttreatment with Aspirin-Triggered Lipoxin A4 Analog Attenuates Lipopolysaccharide-Induced Acute Lung Injury in Mice: The Role of Heme Oxygenase-1," Anesthesia & Analgesia, (2007), vol. 104, No. 2, pp. 369-377.

Karp, Christopher L. et al., "Defective Lipoxin-mediated anti-inflammatory activity in the cystic fibrosis airway," Nature Immunology, (2004), vol. 5, No. 4, pp. 388-392.

Le, Yingying et al., "Biologically Active Peptides Interacting with the G Protein-Coupled Formylpeptide Receptors," Protein & Peptide Letters, (2007), vol. 14, pp. 846-853.

Levy, Bruce D. et al., "Multi-pronged inhibition of airway hyperresponsiveness and inflammation by Lipoxin A4," Nature Medicine, (2002), vol. 8, No. 9, pp. 1018-1023.

Levy, Bruce D. et al., "Lipoxin A4 stable analogs reduce allergic airway responses via mechanisms distinct from CysLT1 receptor antagonism," The Journal of the Federation of American Societies for Experimental Biology, (2007), vol. 21, pp. 3877-3884.

Longshaw, Alistair I. et al., "Design and Synthesis of Potent 'Sulfur-Free' Transition State Analogue Inhibitors of 5'-Methylthioadenosine Nucleosidase and 5'-Methylthioadenosine Phosphorylase," Journal of Medicinal Chemistry, (2010), vol. 53, pp. 6730-6746.

Mamiya, Takayoshi et al., "[Gly14]-Humanin improved the leanring and memory impairment induced by scopolamine in vivo," British Journal of Pharmacology, (2001), vol. 134, pp. 1597-1599.

Miao, Jianting et al., "S14G-Humanin ameliorates Aβ25-35-induced behavioral deficits by reducing neuroinflammatory responses and apoptosis in mice," Neuropeptides, (2008), vol. 42, pp. 557-567.

Planaguma, Anna et al., "Airway LXA4 Receptor Expression Are Decreased in Severe Asthma," American Journal of Respiratory and Critical Care Medicine, (2008), vol. 178, pp. 574-582.

Remington: The Science and Practice of Pharmacy. Twenty-first Edition. Philadelphia, PA. Lippincott Williams & Wilkins, (2005), Part 5: Pharmaceutical Manufacturing, pp. 691-1058.

Schwab, Jan M. et al., "Lipoxins and new lipid mediators in the resolution of inflammation," Current Opinion in Pharmacology, (2006), vol. 6, pp. 414-420.

Sodin-Semrl, S. et al., "Lipoxin A4 Counteracts Synergistic Activation of Human Fibroblast-Like Synoviocytes," International Journal of Immunopathology and Pharmacology, (2004), vol. 17, No. 1, pp. 15-25.

Yazawa, Hiroshi et al., "β Amyloid peptide (Aβ42) is internalized via the G-protein-coupled receptor FPRL1 and forms fibrillar aggregates in macrophages1," The Journal of the Federation of American Societies for Experimental Biology, (2001), vol. 15, pp. 2454-2462.

Ying, Guoguang et al., "Humanin, a Newly Identified Neuroprotective Factor, Uses the G Protein-Coupled Formylpeptide Receptor-Like-1 as a Functional Receptor1," The Journal of Immunology, (2004), vol. 172, pp. 7078-7085.

Zhang, L. et al., "BML-111, a lipoxin receptor agonist, modulates the immune response and reduces the severity of collagen-induced arthritis," Journal of Immunology, (2008), vol. 57, pp. 157-162.

FLUORINATED BRIDGED SPIRO[2.4]HEPTANE DERIVATIVES AS ALX RECEPTOR AGONISTS

CROSS-REFERENCE TO RELATED APPLICATIONS

This application is the U.S. National Phase of International Patent Application No. PCT/IB2013/053976, filed May 15, 2013, which claims the benefit of priority to European Patent Application No. EP 12168322.1, filed May 16, 2012, the contents of each are hereby incorporated by reference in their entireties.

The present invention relates to fluorinated bridged spiro [2.4]heptane derivatives of formula (I) and their use as pharmaceuticals. The invention also concerns related aspects including processes for the preparation of the compounds, pharmaceutical compositions containing one or more compounds of formula (I), and especially their use as ALX receptor (ALXR) agonists.

ALXR (alias Lipoxin A4 Receptor, FPRL1, FPR2; disclosed in WO2003/082314 as nucleotide sequence SEQ ID NO:1 and amino acid sequence SEQ ID NO:2) is a member of the G-protein coupled receptor family. ALXR was found to mediate calcium mobilisation in response to high concentration of the formyl-methionine-leucyl-phenylalanine peptide. Furthermore, a lipid metabolite, lipoxin A4 (LXA4), and its analogues, were found to bind ALXR with high affinity and increase arachidonic acid production and G-protein activation in ALXR transfected cells (Chiang et al., Pharmacol. Rev., 2006, 58, 463-487). The effects of LXA4 have been evaluated in a variety of animal models of diseases; and LXA4 was demonstrated to have potent anti-inflammatory and pro-resolution activities. The disease models where LXA4, or derivatives, or stable analogs, demonstrated in vivo activities are for example dermal inflammation, dorsal air pouch, ischemia/reperfusion injury, peritonitis, colitis, mesangioproliferative nephritis, pleuritis, asthma, cystic fibrosis, sepsis, corneal injury, angiogenesis, periodontitis, carrageenan-induced hyperalgesia, and graft-vs-host disease (GvHD) (Schwab and Serhan, Current Opinion in Pharmacology, 2006, 414-420). Lipoxin A4 inhibited IL-6 expression in human fibroblast-like synoviocytes (Sodin-Semrl et al, *Int J Immunopathol Pharmacol* (2004) 17:15-25) and a stable FPR2 agonist, BML-111, reduced the severity of collagen-induced arthritis (Zhang et al., (2008) *Inflamm Res* 57:157-162) demonstrating a possible use of FPR2 agonists in the treatment of rheumatoid arthritis. Mice with acute lung injury (ALI) showed reduced pulmonary inflammation when treated with stable lipoxin A4 (Jin et al., (2007) *Anesth Analg* 104:369-377). Lower lipoxin A4 levels in severe asthma (Celik et al., (2007) *Clin Exp Allergy* 37:1494-1501; Planaguma et al, (2008) *Am J Respir Crit Care Med* 178:574-582) and improvement of asthma responses in animal models by stable lipoxin A4 analogs (Levy et al., (2002) *Nat Med* 8:1018-1023; Levy et al., (2007) *FASEB J* 21:3877-3884) have been described. In cystic fibrosis it was shown, that the levels of pulmonary lipoxin A4 are decreased both in the lung of cystic fibrosis patients and in animal models of the disease (Karp et al., (2004) *Nat Immunol* 5:388-392); treatment with a stable lipoxin analog improved inflammatory cell accumulation within the diseased lung and reduced body weight loss in the same animals (Karp et al., (2004) *Nat Immunol* 5:388-392). Topical treatment with lipoxin A4 increases re-epithelization and decreases inflammation of the dry corneal surface (Gronert, (2005) *Prostaglandins Leukot Essent Fatty Acids* 73:221-229; Gronert et al., (2005) *J Biol Chem* 280:15267-15278) demonstrating a possible use of FPR2 agonists in the treatment of keratoconjunctivitis sicca. Oral administration of lipoxin A4 analogs reduced the severity of colitis in a mouse model of inflammatory bowel disease (Gewirtz et al., (2002) *Eicosanoids and other Bioactive Lipids in Cancer, Inflammation, and Radiation Injury*, Kluwer Academic/Plenum Publishers, 229-236). ALXR was also identified as a functional receptor of a various number of peptides, including a fragment of the prion protein, a peptide derived from gp120 of the Human Immunodeficiency Virus (HIV)-1$_{LAI}$ strain, and amyloid-beta 1-42 (Ab42) (for review, Le et al., Protein Pept Lett., 2007, 14, 846-853), and has been suggested to participate in the pathogenesis of Alzheimer's Disease (AD) in several crucial ways (Yazawa et al., FASEB J., 2001, 15, 2454-2462). Activation of ALXR on macrophages and microglial cells initiates a G protein-mediated signalling cascade that increases directional cell migration, phagocytosis, and mediator release. These events may account for the recruitment of mononuclear cells to the vicinity of senile plaques in the diseased areas of AD brain where Ab42 is overproduced and accumulated. Although accumulation of leukocytes at the sites of tissue injury may be considered an innate host response aimed at the clearance of noxious agents, activated mononuclear phagocytes also release a variety of substances such as superoxide anions that may be toxic to neurons. Thus, ALXR may mediate pro-inflammatory responses elicited by Ab42 in AD brain and exacerbate disease progression. Further, humanin is a high-affinity ligand for ALXR and is neuroprotective in models of Alzheimer's Disease (Mamiya et al., (2001) *Br J Pharmacol* 134:1597-1599; Ying et al., (2004) *J Immunol* 172:7078-7085; Miao et al., (2008) *Neuropeptides* 42:557-567).

The biological properties of ALXR agonists include, but are not limited to, monocyte/macrophage/microglia/dendritic cell migration/activation, neutrophil migration/activation, regulation of lymphocyte activation, proliferation and differentiation, regulation of inflammation, regulation of cytokine production and/or release, regulation of proinflammatory mediator production and/or release, regulation of immune reaction.

The present invention provides fluorinated bridged spiro [2.4]heptane derivatives, which are non-peptide agonists of human ALX receptor. Other bridged spiro[2.4]heptane derivatives with agonistic activity on human ALX receptor have been disclosed in WO 2010/134014, WO2011/163502, WO2012/066488 and WO2013/009543. Different bridged spiro[2.4]heptane derivatives have been disclosed in WO95/02587. The compounds are useful for the prevention or treatment of diseases, which respond to the modulation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the prevention or treatment of autoimmune diseases and for the modulation of immune responses (especially those elicited by vaccination).

Compared to related compounds claimed in WO2010/134014 the compounds of the present invention show a surprisingly higher bioavailability and a better in vivo plasma exposure when administered orally.

Various embodiments of the invention are presented hereafter:

1) The present invention relates to compounds of formula (I),

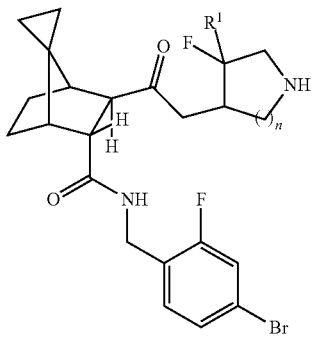

(I)

wherein
n represents 1 or 2; and
R¹ represents hydrogen or fluoro;
and to the salts (in particular pharmaceutically acceptable salts) of such compounds.

The configuration of compounds of formula (I) according to embodiment 1) is such that the two amide substituents are in trans-arrangement and that the cyclopropyl-moiety is in relative proximity to the heterocyclyl-substituted amide (exo-position).

For avoidance of any doubt, compounds of formula (I) are denominated in analogy to the following example:
the pure stereoisomer of structure

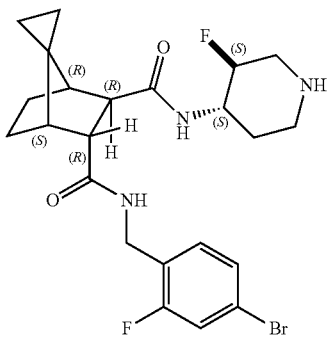

is denominated (1S,2R,3R,4R)—N²-(4-bromo-2-fluorobenzyl)-N³-((3S,4S)-3-fluoropiperidin-4-yl)spiro[bicyclo[2.2.1]heptane-7,1'-cyclopropane]-2,3-dicarboxamide The compounds of formula (I) according to embodiment 1) may contain one or more stereogenic or asymmetric centers, such as one or more asymmetric carbon atoms. Substituents at a double bond may be present in the (Z)- or (E)-configuration unless indicated otherwise. The compounds of formula (I) may thus be present as mixtures of stereoisomers or preferably as pure stereoisomers. Mixtures of stereoisomers may be separated in a manner known to a person skilled in the art.

2) A preferred embodiment of the invention relates to compounds of formula (I) according to embodiment 1) which are also compounds of formula (I$_{ST1}$),

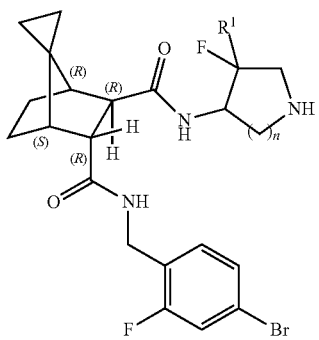

(I$_{ST1}$)

wherein
n represents 1 or 2; and
R¹ represents hydrogen or fluoro;
and to the salts (in particular pharmaceutically acceptable salts) of such compounds.

3) A further embodiment of the invention relates to compounds of formula (I) according to any one of embodiments 1) or 2), wherein
n represents 1;
and to the salts (in particular pharmaceutically acceptable salts) of such compounds.

4) A further embodiment of the invention relates to compounds of formula (I) according to any one of embodiments 1) or 2), wherein
n represents 2;
and to the salts (in particular pharmaceutically acceptable salts) of such compounds.

5) A further embodiment of the invention relates to compounds of formula (I) according to any one of embodiments 1) to 4), wherein
R¹ represents hydrogen;
and to the salts (in particular pharmaceutically acceptable salts) of such compounds.

6) A further embodiment of the invention relates to compounds of formula (I) according to any one of embodiments 1) to 4), wherein
R¹ represents fluoro;
and to the salts (in particular pharmaceutically acceptable salts) of such compounds.

7) A further embodiment of the invention relates to compounds of formula (I) according to any one of embodiments 1) to 4), wherein
R¹ represents hydrogen and the two stereogenic centers at the heterocyclyl group, which is attached to the amide nitrogen-atom, are relative to each other in trans-configuration; and to the salts (in particular pharmaceutically acceptable salts) of such compounds.

8) A further embodiment of the invention relates to compounds of formula (I) according to any one of embodiments 1) to 4) or 7), wherein
R¹ represents hydrogen and the carbon-atom attached to R¹ is (S)-configurated;
and to the salts (in particular pharmaceutically acceptable salts) of such compounds.

9) A further embodiment of the invention relates to compounds of formula (I) according to any one of embodiments 1) to 4) or 7), wherein
R¹ represents hydrogen and the carbon-atom attached to R¹ is (R)-configurated; and to the salts (in particular pharmaceutically acceptable salts) of such compounds.

10) A further embodiment of the invention relates to compounds of formula (I) according to any one of embodiments 1) to 9), wherein
the carbon-atom of the heterocyclyl-group, which is attached to the amide nitrogen-atom, is (S)-configurated;
and to the salts (in particular pharmaceutically acceptable salts) of such compounds.

11) A further embodiment of the invention relates to compounds of formula (I) according to any one of embodiments 1) to 9), wherein
the carbon-atom of the heterocyclyl-group, which is attached to the amide nitrogen-atom, is (R)-configurated;
and to the salts (in particular pharmaceutically acceptable salts) of such compounds.

12) Preferred compounds of formula (I) as defined in embodiment 1) are selected from the group consisting of:
(1S,2R,3R,4R)—$N^2$-(4-bromo-2-fluorobenzyl)-$N^3$-((3S, 4S)-3-fluoropiperidin-4-yl)spiro[bicyclo[2.2.1]heptane-7,1'-cyclopropane]-2,3-dicarboxamide;
(1S,2R,3R,4R)—$N^2$-(4-bromo-2-fluorobenzyl)-$N^3$-((3R, 4R)-3-fluoropiperidin-4-yl)spiro[bicyclo[2.2.1]heptane-7,1'-cyclopropane]-2,3-dicarboxamide;
(1S,2R,3R,4R)—$N^2$-(4-bromo-2-fluorobenzyl)-$N^3$-(cis-3-fluoropiperidin-4-yl)spiro[bicyclo[2.2.1]heptane-7,1'-cyclopropane]-2,3-dicarboxamide;
(1S,2R,3R,4R)—$N^2$-(4-bromo-2-fluorobenzyl)-$N^3$-(3,3-difluoropiperidin-4-yl)spiro[bicyclo[2.2.1]heptane-7,1'-cyclopropane]-2,3-dicarboxamide;
(1S,2R,3R,4R)—$N^2$-(4-Bromo-2-fluorobenzyl)-$N^3$-(cis-4-fluoropyrrolidin-3-yl)spiro[bicyclo[2.2.1]heptane-7,1'-cyclopropane]-2,3-dicarboxamide; and
(1S,2R,3R,4R)—$N^2$-(4-Bromo-2-fluorobenzyl)-$N^3$-(trans-4-fluoropyrrolidin-3-yl)spiro[bicyclo[2.2.1]heptane-7,1'-cyclopropane]-2,3-dicarboxamide;
or salts (in particular pharmaceutically acceptable salts) of such compounds; it is to be understood for any of the above listed compounds, that a stereogenic center, which is not specifically assigned, may be in absolute (R)- or absolute (S)-configuration. Notably, compounds containing more than one stereogenic center may be at each stereogenic center, which is not specifically assigned, in absolute (R)- or absolute (S)-configuration; for example a compound listed as (1S,2R, 3R,4R)—$N^2$-(4-bromo-2-fluorobenzyl)-$N^3$-(cis-3-fluoropiperidin-4-yl)spiro[bicyclo[2.2.1]heptane-7,1'-cyclopropane]-2,3-dicarboxamide may be (1S,2R,3R,4R)—$N^2$-(4-bromo-2-fluorobenzyl)-$N^3$-((3S,4R)-3-fluoropiperidin-4-yl)spiro[bicyclo[2.2.1]heptane-7,1'-cyclopropane]-2,3-dicarboxamide, (1S,2R,3R,4R)—$N^2$-(4-bromo-2-fluorobenzyl)-$N^3$-((3R,4S)-3-fluoropiperidin-4-yl)spiro[bicyclo[2.2.1]heptane-7,1'-cyclopropane]-2,3-dicarboxamide or any mixture thereof.

It is well understood that the invention relates to compounds according to embodiment 1); or according to embodiment 1) limited by the features of an embodiment dependent on embodiment 1; or according to embodiment 1) limited by the features of a cascade of dependent embodiments e.g. in the form of "embodiment 3) depending on embodiment 2) depending on embodiment 1)". In case of an embodiment depending on more than one other embodiment, it is understood that each combination is specifically disclosed. Also, in case an embodiment is dependent on more than one other embodiment and one or more of said other embodiments are themselves dependent on one or more further embodiments, it is understood that each combination is specifically disclosed if obtainable with regard to the given dependencies and multiple dependencies. Notably, embodiments resulting from cascades of more than three embodiments depending on each other may be construed under observance of the given dependencies and multiple dependencies and are thus intended to be specifically disclosed. Examples of embodiments which are possible based on the dependencies of the embodiments 1) to 12) as disclosed hereinabove and which are therefore intended and herewith specifically disclosed in individualized form are:

1, 2+1, 3+1, 3+2+1, 4+1, 4+2+1, 5+1, 5+2+1, 5+3+1, 5+3+2+1, 5+4+1, 5+4+2+1, 6+1, 6+2+1, 6+3+1, 6+3+2+1, 6+4+1, 6+4+2+1, 7+1, 7+2+1, 7+3+1, 7+3+2+1, 7+4+1, 7+4+2+1, 8+1, 8+2+1, 8+3+1, 8+3+2+1, 8+4+1, 8+4+2+1, 8+7+1, 8+7+2+1, 8+7+3+1, 8+7+3+2+1, 8+7+4+1, 8+7+4+2+1, 9+1, 9+2+1, 9+3+1, 9+3+2+1, 9+4+1, 9+4+2+1, 9+7+1, 9+7+2+1, 9+7+3+1, 9+7+3+2+1, 9+7+4+1, 9+7+4+2+1, 10+1, 10+2+1, 10+3+1, 10+3+2+1, 10+4+1, 10+4+2+1, 10+5+1, 10+5+2+1, 10+5+3+1, 10+5+3+2+1, 10+5+4+1, 10+5+4+2+1, 10+6+1, 10+6+2+1, 10+6+3+1, 10+6+3+2+1, 10+6+4+1, 10+6+4+2+1, 10+7+1, 10+7+2+1, 10+7+3+1, 10+7+3+2+1, 10+7+4+1, 10+7+4+2+1, 10+8+1, 10+8+2+1, 10+8+3+1, 10+8+3+2+1, 10+8+4+1, 10+8+4+2+1, 10+8+7+1, 10+8+7+2+1, 10+8+7+3+1, 10+8+7+3+2+1, 10+8+7+4+1, 10+8+7+4+2+1, 10+9+1, 10+9+2+1, 10+9+3+1, 10+9+3+2+1, 10+9+4+1, 10+9+4+2+1, 10+9+7+1, 10+9+7+2+1, 10+9+7+3+1, 10+9+7+3+2+1, 10+9+7+4+1, 10+9+7+4+2+1, 11+1, 11+2+1, 11+3+1, 11+3+2+1, 11+4+1, 11+4+2+1, 11+5+1, 11+5+2+1, 11+5+3+1, 11+5+3+2+1, 11+5+4+1, 11+5+4+2+1, 11+6+1, 11+6+2+1, 11+6+3+1, 11+6+3+2+1, 11+6+4+1, 11+6+4+2+1, 11+7+1, 11+7+2+1, 11+7+3+1, 11+7+3+2+1, 11+7+4+1, 11+7+4+2+1, 11+8+1, 11+8+2+1, 11+8+3+1, 11+8+3+2+1, 11+8+4+1, 11+8+4+2+1, 11+8+7+1, 11+8+7+2+1, 11+8+7+3+1, 11+8+7+3+2+1, 11+8+7+4+1, 11+8+7+4+2+1, 11+9+1, 11+9+2+1, 11+9+3+1, 11+9+3+2+1, 11+9+4+1, 11+9+4+2+1, 11+9+7+1, 11+9+7+2+1, 11+9+7+3+1, 11+9+7+3+2+1, 11+9+7+4+1, 11+9+7+4+2+1 and 12+1;

wherein in the list above the numbers refer to the embodiments according to their numbering provided hereinabove whereas "+" indicates the dependency from another embodiment. The different individualized embodiments are separated by commas. In other words, "3+2+1" for example refers to embodiment 3) depending on embodiment 2) depending on embodiment 1), i.e. embodiment "3+2+1" corresponds to embodiment 1) further limited by the features of embodiments 2) and 3).

The term "heterocyclyl", used alone or in combination, means pyrrolidinyl or piperidinyl.

The present invention also includes isotopically labelled, especially $^2$H (deuterium) labelled compounds of formula (I), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

The term "pharmaceutically acceptable salts" refers to non-toxic, inorganic or organic acid and/or base addition salts, Lit. e.g. "Salt selection for basic drugs", *Int. J. Pharm.* (1986), 33, 201-217.

Where the plural form is used for compounds, salts, pharmaceutical compositions, diseases and the like, this is intended to mean also a single compound, salt, or the like.

The compounds of formula (I) according to any one of embodiments 1) to 12), or pharmaceutically acceptable salts thereof, are suitable for use as medicaments. In particular, compounds of formula (I) modulate the ALX receptor, i.e. they act as ALX receptor agonists, and are useful for the prevention or treatment of diseases which respond to the activation of the ALX receptor such as inflammatory diseases, obstructive airway diseases, allergic conditions, HIV-mediated retroviral infections, cardiovascular disorders, neuroinflammation, neurological disorders, pain, prion-mediated diseases and amyloid-mediated disorders (especially Alzheimer's disease); in addition they are useful for the modulation of immune responses (especially those elicited by vaccination). Especially, compounds of formula (I) are useful for the prevention or treatment of diseases such as inflammatory diseases, obstructive airway diseases, allergic conditions, cardiovascular disorders, neuroinflammation, neurological disorders, pain, prion-mediated diseases and amyloid-mediated disorders (especially Alzheimer's disease).

In particular, the compounds of formula (I) according to any one of embodiments 1) to 12), or pharmaceutically acceptable salts thereof, are suitable for the prevention or treatment of diseases selected from inflammatory diseases, obstructive airway diseases and allergic conditions.

Inflammatory diseases, obstructive airway diseases and allergic conditions include, but are not limited to, one, several or all of the following groups of diseases and disorders:

1) Acute lung injury (ALI); adult/acute respiratory distress syndrome (ARDS); chronic obstructive pulmonary, airway or lung disease (COPD, COAD or COLD), including chronic bronchitis or dyspnea associated therewith; emphysema; as well as exacerbation of airway hyper reactivity consequent to other drug therapy, in particular other inhaled drug therapy. Especially, inflammatory diseases, obstructive airway diseases and allergic conditions include COPD, COAD and COLD.

2) Further inflammatory diseases, obstructive airway diseases and allergic conditions include bronchitis of whatever type or genesis.

3) Further inflammatory diseases, obstructive airway diseases and allergic conditions include bronchiectasis, and pneumoconiosis of whatever type or genesis.

4) Further inflammatory diseases, obstructive airway diseases and allergic conditions include asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection.

5) In a further embodiment the compounds of formula (I) according to any one of embodiments 1) to 12), or pharmaceutically acceptable salts thereof, are particularly suitable for the prevention or treatment of inflammatory diseases. Inflammatory diseases include one, several or all of the following groups of diseases and disorders:

5a) In particular, inflammatory diseases refer to neutrophil related disorders, especially neutrophil related disorders of the airway including hyper-neutrophilia as it affects the airway and/or lungs. Further neutrophil related disorders also include periodontitis, glomerulonephritis, and cystic fibrosis.

5b) Further inflammatory diseases include skin diseases such as psoriasis, contact dermatitis, atopic dermatitis, dermatitis herpetiformis, scleroderma, hypersensitivity angiitis, urticaria, lupus erythematosus, and epidermolysis.

5c) Further inflammatory diseases also relate to diseases or conditions having an inflammatory component. Diseases or conditions having an inflammatory component include, but are not limited to, diseases and conditions affecting the eye such as uveitis (anterior, intermediate and posterior), Behçet syndrome uveitis, conjunctivitis, keratoconjunctivitis sicca, Sjögren syndrome keratoconjunctivitis sicca, and vernal conjunctivitis (and especially conjunctivitis, keratoconjunctivitis sicca, and vernal conjunctivitis); diseases affecting the nose including rhinitis and allergic rhinitis (and especially allergic rhinitis); and inflammatory diseases in which autoimmune reactions are implicated or which have an autoimmune component or aetiology, such as systemic lupus erythematosus, ankylosing spondylitis, Behçet syndrome, Sjögren syndrome, polychondritis, scleroderma, Wegener granulamatosis, dermatomyositis, chronic active hepatitis, myasthenia gravis, Stevens-Johnson syndrome, idiopathic sprue, autoimmune inflammatory bowel disease (e.g. ulcerative colitis and Crohn's disease), endocrine opthalmopathy, chronic hypersensitivity pneumonitis, primary billiary cirrhosis, keratoconjunctivitis sicca and vernal keratoconjunctivitis, interstitial lung fibrosis, psoriatic arthritis and glomerulonephritis.

5d) Further inflammatory diseases in which autoimmune reactions are implicated or which have an autoimmune component or aetiology include rheumatoid arthritis, Hashimoto's thyroid and diabetes type I or II.

Further, the compounds of formula (I) according to any one of embodiments 1) to 12), or pharmaceutically acceptable salts thereof, are suitable for the prevention or treatment of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation, particularly in the treatment of acute or chronic allo- and xenograft rejection or in the transplantation of insulin producing cells, e.g. pancreatic islet cells.

Further, the compounds of formula (I) according to any one of embodiments 1) to 12), or pharmaceutically acceptable salts thereof, are suitable for the prevention or treatment of HIV-mediated retroviral infections.

HIV-mediated retroviral infections include, but are not limited to, one, several or all of the groups of diseases and disorders caused by HIV-1 and HIV-2 strains such as GUN-4v, GUN-7 wt, AG204, AG206, AG208, HCM305, HCM308, HCM342, mSTD104, and HCM309.

Further, the compounds of formula (I) according to any one of embodiments 1) to 12), or pharmaceutically acceptable salts thereof, are suitable for the prevention or treatment of cardiovascular disorders.

Cardiovascular disorders refer to one or more disease states of the cardiovascular tree (including the heart) and to diseases of dependent organs. Disease states of the cardiovascular tree and diseases of dependent organs include, but are not limited to, disorders of the heart muscle (cardiomyopathy or myocarditis) such as idiopathic cardiomyopathy, metabolic cardiomyopathy which includes diabetic cardiomyopathy, alcoholic cardiomyopathy, drug-induced cardiomyopathy, ischemic cardiomyopathy, and hypertensive cardiomyopathy; atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries; toxic, drug-induced, and metabolic (including hypertensive and/or diabetic) disorders of small blood vessels (microvascular disease) such as the retinal arterioles, the glomerular arterioles, the vasa nervorum, cardiac arterioles, and associated capillary beds of the eye, the kidney, the heart, and the central and peripheral nervous systems; and, plaque rupture of atheromatous lesions of major blood vessels such as the aorta, the coronary arteries, the carotid arteries, the cerebrovascular arteries, the renal arteries, the iliac arteries, the femoral arteries and the popliteal arteries.

Further, the compounds of formula (I) according to any one of embodiments 1) to 12), or pharmaceutically acceptable salts thereof, are suitable for the prevention or treatment of neuroinflammation. Neuroinflammation refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as nitric oxide synthase production and nitric oxide accumulation, acute phase proteins, loss of synaptophysin and Post Synaptic Density-95 Protein (PSD-95), components of the complement cascade, loss or reduction of synaptic function, protein kinase activity (e.g., death associated protein kinase activity), behavioral deficits, cell damage (e.g., neuronal cell damage), cell death (e.g., neuronal cell death), and/or amyloid β deposition of amyloid plaques.

Further, the compounds of formula (I) according to any one of embodiments 1) to 12), or pharmaceutically acceptable salts thereof, are suitable for the prevention or treatment of neurological disorders.

In particular, neurological disorders include, but are not limited to, epilepsy, stroke, cerebral ischemia, cerebral palsy, relapsing remitting multiple sclerosis, progressive multiple sclerosis, neuromyelitis optica, clinically isolated syndrome, Alpers' disease, amyotrophic lateral sclerosis (ALS), senile dementia, dementia with Lewy bodies, Rett syndrome, spinal cord trauma, traumatic brain injury, trigeminal neuralgia, chronic inflammatory demyelinating polyneuropathy, Guillain-Barré syndrome, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea (and especially epilepsy, stroke, cerebral ischemia, cerebral palsy, relapsing remitting multiple sclerosis, progressive multiple sclerosis, Alpers' disease, amyotrophic lateral sclerosis (ALS), senile dementia, dementia with Lewy bodies, Rett syndrome, spinal cord trauma, traumatic brain injury, trigeminal neuralgia, glossopharyngeal neuralgia, Bell's palsy, myasthenia gravis, muscular dystrophy, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies, mild cognitive decline, cognitive decline, Alzheimer's disease, Parkinson's disease, and Huntington's chorea).

Further, the compounds of formula (I) according to any one of embodiments 1) to 12), or pharmaceutically acceptable salts thereof, are suitable for the prevention or treatment of pain. Pain includes, but is not limited to, neuropathic pain exemplified by conditions such as diabetic neuropathy, postherpetic neuralgia, trigeminal neuralgia, painful diabetic polyneuropathy, post-stroke pain, post-amputation pain, myelopathic or radiculopathic pain, atypical facial pain and causalgia-like syndromes.

Further, the compounds of formula (I) according to any one of embodiments 1) to 12), or pharmaceutically acceptable salts thereof, are suitable for the prevention or treatment of prion-mediated diseases. Prion-mediated diseases, also known as transmissible spongiform encephalopathies (TSEs), include, but are not limited to, kuru, Gerstmann-Sträussler-Scheinker syndrome (GSS), Fatal Familial Insomnia (FFI) and Creutzfeldt-Jakob Disease (CJD).

Further, the compounds of formula (I) according to any one of embodiments 1) to 12), or pharmaceutically acceptable salts thereof, are suitable for the treatment of amyloid-mediated disorders. Amyloid-mediated disorders are defined as diseases and disorders, that are caused by or associated with amyloid or amyloid-like proteins. Diseases and disorders caused by or associated with amyloid or amyloid-like proteins include, but are not limited to, Alzheimer's Disease (AD), including diseases or conditions characterized by a loss of cognitive memory capacity such as, for example, mild cognitive impairment (MCI); dementia with Lewy bodies; Down's syndrome; cerebral hemorrhage with amyloidosis. In another embodiment, diseases and disorders caused by or associated with amyloid or amyloid-like proteins include progressive supranuclear palsy, amyloid light chain amyloidosis, familial amyloid neuropathies, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis (and especially progressive supranuclear palsy, multiple sclerosis, Creutzfeld Jakob disease, Parkinson's disease, HIV-related dementia, Amyotrophic Lateral Sclerosis (ALS), inclusion-body myositis (IBM), Adult Onset Diabetes, and senile cardiac amyloidosis).

Further, the compounds of formula (I) according to any one of embodiments 1) to 12), or pharmaceutically acceptable salts thereof, are suitable for the modulation of immune responses.

The modulation of immune responses includes, but is not limited to, methods based on the administration to a subject a composition of at least one antigen and at least one compound of formula (I) according to any one of embodiments 1) to 12), or pharmaceutically acceptable salts thereof. In some cases, the antigen-containing composition is administrated first, followed by administration of a composition of at least one compounds of formula (I) according to any one of embodiments 1) to 12), or pharmaceutically acceptable salts thereof. In other cases, the antigen-containing composition is administrated last. The different compositions may be administrated simultaneously, closely in sequence, or separated in time. Those methods and compositions are provided for therapeutic and prophylactic immunisation (i.e., the deliberate provocation, enhancement, intensification or modulation of an adaptative and/or innate immune response). Particular advantages may include one or more of the following:

1) An accelerated immune response following administration of at least one compound of formula (I) according to any one of embodiments 1) to 12), or pharmaceutically acceptable salts thereof, and the antigen, as compared to sole administration of the antigen;

2) A greater sensitivity to small amounts of antigen (e.g., toxin or pathogen) or antigens that do not habitually induce strong immune responses; and
3) More effective anti-tumor therapies.

Further, the compounds of formula (I) according to any one of embodiments 1) to 12), or pharmaceutically acceptable salts thereof, are suitable for the prevention or treatment of cystic fibrosis, pulmonary fibrosis, pulmonary hypertension, wound healing, diabetic nephropathy, reduction of inflammation in transplanted tissue, inflammatory diseases caused by pathogenic organisms.

Especially, compounds of formula (I) according to any one of embodiments 1) to 12), or pharmaceutically acceptable salts thereof, are suitable for the prevention or treatment of diseases selected from one, several or all of the following groups of diseases and disorders:
1) Inflammatory diseases, obstructive airway diseases and allergic conditions such as acute lung injury (ALI); adult/acute respiratory distress syndrome (ARDS); chronic obstructive pulmonary, airway or lung disease (COPD, COAD or COLD), including chronic bronchitis or dyspnea associated therewith; and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection (and especially acute lung injury (ALI); adult/acute respiratory distress syndrome (ARDS); and asthma of whatever type or genesis, including intrinsic (non-allergic) asthma and extrinsic (allergic) asthma, mild asthma, moderate asthma, severe asthma, bronchitic asthma, exercise-induced asthma, occupational asthma and induced asthma following bacterial infection);
2) Inflammatory diseases such as neutrophil related disorders, especially neutrophil related disorders of the airway including hyper-neutrophilia as it affects the airway and/or lungs; periodontitis; glomerulonephritis; cystic fibrosis; and skin diseases such as psoriasis, contact dermatitis, atopic dermatitis, dermatitis herpetiformis, scleroderma, hypersensitivity angiitis, urticaria, lupus erythematosus, and epidermolysis;
3) Diseases having an inflammatory component such as diseases and conditions affecting the eye such as conjunctivitis, keratoconjunctivitis sicca, and vernal conjunctivitis; inflammatory disease in which autoimmune reactions are implicated or which have an autoimmune component or aetiology; and autoimmune inflammatory bowel disease (e.g. ulcerative colitis and Crohn's disease);
4) HIV-mediated retroviral infections such as diseases and disorders caused by HIV-1 and HIV-2 strains such as GUN-4v, GUN-7 wt, AG204, AG206, AG208, HCM305, HCM308, HCM342, mSTD104, and HCM309;
5) Neuroinflammation which refers to cell signalling molecule production, activation of glia or glial activation pathways and responses, proinflammatory cytokines or chemokines, activation of astrocytes or astrocyte activation pathways and responses, activation of microglia or microglial activation pathways and responses, oxidative stress-related responses such as amyloid 13 deposition of amyloid plaques;
6) Neurological disorders such as stroke, cerebral ischemia, Alzheimer's disease, and Parkinson's disease;
7) Prion-mediated diseases, also known as transmissible spongiform encephalopathies (TSEs), such as kuru, Gerstmann-Straussler-Scheinker syndrome (GSS), Fatal Familial Insomnia (FFI) and Creutzfeldt-Jakob Disease (CJD);
8) Amyloid-mediated disorders;
9) Cystic fibrosis, wound healing and inflammatory diseases caused by pathogenic organisms.

Most preferably, compounds of formula (I) according to any one of embodiments 1) to 12), or pharmaceutically acceptable salts thereof, are suitable for the prevention or treatment of diseases selected from the group consisting of acute lung injury (ALI); asthma; cystic fibrosis; keratoconjunctivitis sicca; inflammatory bowel disease; rheumatoid arthritis; and Alzheimer's Disease.

The invention also relates to the use of a compound of formula (I) according to any one of embodiments 1) to 12) for the preparation of pharmaceutical compositions for the treatment and/or prophylaxis of the above-mentioned diseases.

The present invention also relates to pharmaceutically acceptable salts and to pharmaceutical compositions and formulations of compounds of formula (I) according to any one of embodiments 1) to 12).

A pharmaceutical composition according to the present invention contains at least one compound of formula (I) according to any one of embodiments 1) to 12) (or a pharmaceutically acceptable salt thereof) as the active agent and optionally carriers and/or diluents and/or adjuvants.

The compounds of formula (I) according to any one of embodiments 1) to 12) and their pharmaceutically acceptable salts can be used as medicaments, e.g. in the form of pharmaceutical compositions for enteral (such as especially oral) or parenteral (including topical application or inhalation) administration.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention or treatment of a disease or disorder mentioned herein comprising administering to a subject a pharmaceutically active amount of a compound of formula (I) according to any one of embodiments 1) to 12), or a pharmaceutically acceptable salt thereof.

Any reference to a compound of formula I or $I_{ST1}$ in this text is to be understood as referring also to the salts (and especially the pharmaceutically acceptable salts) of such compounds, as appropriate and expedient. The preferences indicated for the compounds of formula I of course apply mutatis mutandis to the compounds of formula $I_{ST1}$ as well as to the salts and pharmaceutically acceptable salts of the compounds of formula I or of formula $I_{ST1}$. The same applies to these compounds as medicaments, to pharmaceutical compositions containing these compounds as active principles or to the uses of these compounds for the manufacture of a medicament for the treatment of the diseases according to this invention.

Unless used regarding temperatures, the term "about" (or alternatively "around") placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively "around") placed before a temperature "Y"

refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

If not indicated otherwise, the generic groups $R^1$ and n are as defined for formula (I). Other abbreviations used are defined in the experimental section.

A. Synthesis of Final Products

The compounds of formula (I) can be prepared from compounds of structure 1 by BOC deprotection of compounds of structure 1 as described in the general procedures below (experimental part).

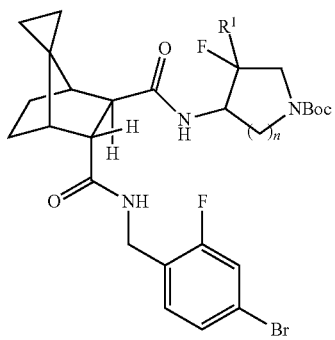

Structure 1

The compounds of structure 1 can be prepared from the carboxylic acid of structure 2 by reaction with an appropriate amine using standard amide coupling conditions such as EDC/HOBt, or DCC/HOAt, or PyBOP, or HATU in the presence of a base such as DIPEA or DMAP or a combination of both at a temperature ranging from rt to about 60° C. in a suitable solvent such as $CH_2Cl_2$ or THF/DMF. Alternatively, the compounds of formula (I) can be prepared by coupling the carboxylic acid of structure 2 with an appropriate amine using $POCl_3$ in a suitable solvent such as DCE/pyridine (1:1). Alternatively, the compounds of formula (I) can be prepared by coupling an appropriate amine with the carboxylic acid of structure 2 via formation of the acyl chloride (using standard conditions such as oxalyl chloride and a catalytic amount of DMF in a solvent such as toluene or $CH_2Cl_2$).

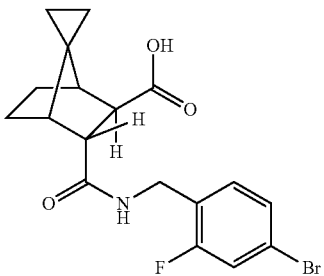

Structure 2

The carboxylic acid of structure 2 can be synthesized according to the procedure described in the experimental part (see also WO2010/134014).

The appropriate amines are either commercially available or can be synthesized by the method given below or in the experimental part.

The amines trans-tert-butyl 4-amino-3-fluoropiperidine-1-carboxylate and cis-tert-butyl 4-amino-3-fluoropiperidine-1-carboxylate can be synthesized following a known procedure (WO2005/090330).

Racemic tert-butyl 4-amino-3,3-difluoropiperidine-1-carboxylate can be prepared from 1-benzyl-3,3-difluoropiperidine-4,4-diol (WO2008/121687 and WO2005/040120) with the following synthetic sequence: 1) reduction of the diol with a reducing agent such as $NaBH_4$ in a solvent like THF at a temperature ranging from 0° C. to rt; 2) protective group exchange from benzyl to Boc by hydrogenation of 1-benzyl-3,3-difluoropiperidin-4-ol in the presence of a catalyst such as $Pd(OH)_2$ in a solvent such as EtOH at rt, followed by Boc protection with di-tert-butyl dicarbonate in a solvent such as $CH_2Cl_2$ at rt; 3) oxidation of the hydroxyl group with an oxidating agent such as Dess-Martin periodinane in an appropriate solvent such as $CH_2Cl_2$ at a temperature ranging from 0° C. to rt; 4) reductive amination with benzylamine and a suitable reducing agent such as $NaBH(OAc)_3$ or $NaBH_4$ in an appropriate solvent like $CH_2Cl_2$ at rt; and 5) cleavage of the benzyl protecting group by hydrogenation using a metal such as Pd in a solvent such as MeOH at rt.

The synthesis of trans-tert-butyl 3-amino-4-fluoropyrrolidine-1-carboxylate, cis-tert-butyl 3-amino-4-fluoropyrrolidine-1-carboxylate, and tert-butyl 4-amino-3,3-difluoropyrrolidine-1-carboxylate is outlined in Scheme 1.

trans-tert-Butyl 3-amino-4-fluoropyrrolidine-1-carboxylate can be prepared from trans-tert-butyl 3-azido-4-hydroxypyrrolidine-1-carboxylate (J. Med. Chem. 2010, 53, 6730-6746) by fluorination using a suitable fluorinating agent such as DAST in an appropriate solvent such as $CH_2Cl_2$ at a temperature ranging from −78° C. to 0° C., followed by reduction of the azido group to the corresponding amine using $PPh_3$/$H_2O$ in a suitable solvent such as THF at a temperature of about 60° C., or hydrogenation using a catalyst such as Pd or $PtO_2$ in a suitable solvent such as MeOH at rt.

cis-tert-Butyl 3-amino-4-fluoropyrrolidine-1-carboxylate can be obtained using the following sequence: 1) activation of the hydroxyl group of trans-tert-butyl 3-azido-4-hydroxypyrrolidine-1-carboxylate for example by tosylation using TsCl in pyridine at a temperature ranging from about 5° C. to rt; 2) fluorination with a suitable fluorinating agent such as n-tributylammonium fluoride in an appropriate solvent such as THF at a temperature ranging from rt to about 65° C.; and 3) reduction of the azido group to the corresponding amine using $PPh_3$/$H_2O$ in a suitable solvent such as THF at a temperature of about 60° C., or hydrogenation using a catalyst such as Pd or $PtO_2$ in a suitable solvent such as MeOH at rt.

tert-Butyl 4-amino-3,3-difluoropyrrolidine-1-carboxylate can be obtained in three synthetic steps starting from trans-tert-butyl 3-azido-4-hydroxypyrrolidine-1-carboxylate: 1) oxidation of the hydroxyl group using for example Swern's conditions i.e. oxalyl chloride and DMSO in a suitable solvent such as $CH_2Cl_2$ at a temperature ranging from $-78°$ C. to $-60°$ C., or using Dess-Martin periodinane in a suitable solvent such as $CH_2Cl_2$ or THF at a temperature ranging from $0°$ C. to rt; 2) fluorination using a suitable fluorinating agent such as DAST or Deoxofluor in an appropriate solvent such as $CH_2Cl_2$ at a temperature ranging from $0°$ C. to rt; and 3) reduction of the azido group to the corresponding amine using $PPh_3/H_2O$ in a suitable solvent such as THF at a temperature of about $60°$ C., or hydrogenation using a catalyst such as Pd or $PtO_2$ in a suitable solvent such as MeOH at rt.

Enantiopure trans-tert-butyl 3-amino-4-fluoropyrrolidine-1-carboxylate, cis-tert-butyl 3-amino-4-fluoropyrrolidine-1-carboxylate, and tert-butyl 4-amino-3,3-difluoropyrrolidine-1-carboxylate can be prepared starting from enantiopure trans-tert-butyl 3-azido-4-hydroxypyrrolidine-1-carboxylate, which can be obtained via an asymmetric ring opening reaction of the corresponding epoxide using for example Jacobsen's salen catalyst (WO2006/114401). Depending on the configuration of the catalyst one or the other enantiomer might be obtained.

Scheme 1

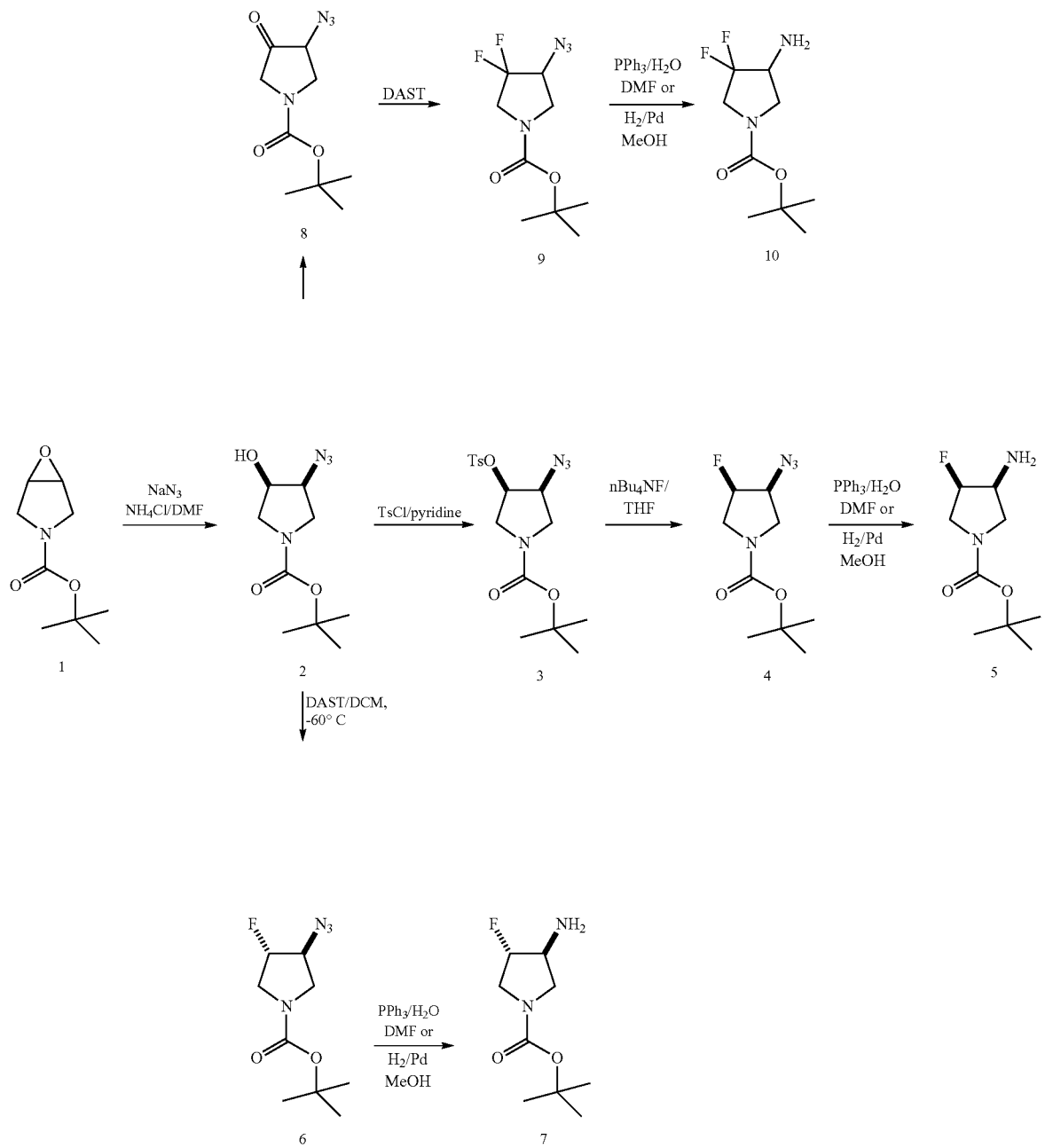

EXPERIMENTAL PART

Abbreviations (as Used Herein and in the Description Above)

Ac acetyl
aq. aqueous
Boc tert-butoxycarbonyl
bp boiling point
(n-)Bu butyl
ca. about
COAD chronic obstructive airway disease
COLD chronic obstructive lung disease
COPD chronic obstructive pulmonary disease
DAD diode array detector
DAST (diethylamino)sulfur trifluoride
DCC N,N'-dicyclohexylcarbodiimide
DCE 1,2-dichloroethane
DEA diethylamine
DIPEA diisopropylethylamine
DMAP 4-N,N-dimethylaminopyridine
DMEM dulbecco's modified eagle's medium
DMF dimethylformamide
DMSO dimethylsulfoxide
EA ethyl acetate
$EC_{50}$ half maximal effective concentration
EDC N-(3-dimethylaminopropyl)-W-ethyl-carbodiimide
ELSD evaporative light-scattering detection
eq. equivalent(s)
Et ethyl
Ether or $Et_2O$ diethylether
$Et_3N$ triethylamine
EtOH ethanol
FC flash column chromatography on silica gel
FLIPR fluorescence imaging plate reader
FPRL1 formyl-peptide receptor like-1
FPRL2 formyl-peptide receptor like-2
GSH Glutathione
h hour(s)
HATU 2-(7-aza-1H-benzotriazol-1-yl)-1,1,3,3-tetramethyluronium hexafluorophosphate
HEPES 4-(2-hydroxyethyl)-1-piperazineethanesulfonic acid
hept heptane
HIV human immunodeficiency virus
HOBt hydroxybenzotriazole
HOAt 7-aza-1-hydroxybenzotriazole
HPLC high performance liquid chromatography
i.p. intraperitoneal
i.v. intravenous
LC-MS liquid chromatography-mass spectrometry
lem emission wavelength
lex excitation wavelength
Me methyl
MeOH methanol
min minute(s)
mM millimolar
μM micromolar
MS mass spectrometry
nm nanometer
nM nanomolar
NMR nuclear magnetic resonance
OAc acetate
org. organic
p para
p.o. per os
PyBOP benzotriazol-1-yl-oxy-tris-pyrrolidino-phosphonium-hexafluoro-phosphate
rf retention factor
rpm rotation per minute
rt room temperature
sat. Saturated
s.c. subcutaneous
t-Bu tert-butyl
TFA trifluoroacetic acid
THF tetrahydrofuran
TLC thin layer chromatography
TMS trimethyl-silyl
$t_R$ retention time
TsCl tosyl chloride
UI International Unit
UV ultra violet
Vis visible
I Chemistry
  General.

All temperatures are stated in degrees Celsius (° C.). Unless otherwise indicated, the reactions take place at rt.

Analytical thin layer chromatography (TLC) was performed with 0.2 mm plates: Merck, Silica gel 60 $F_{254}$. Preparative thin layer chromatography (TLC) was performed with 0.2 or 0.5 mm plates: Merck, Silica gel 60 $F_{254}$. Detection was done with UV or with a solution of $KMnO_4$ (3 g), $K_2CO_3$ (20 g), NaOH 5% (3 mL) and $H_2O$ (300 mL) with subsequent heating.

Flash column chromatography (FC) and filtration were performed using silica gel 60 Merck (0.063-0.200 mm) or Macherey-Nagel silica gel (0.063-0.200 mm): elution with EA, $Et_2O$, hept, hexane, petroleum ether, $CH_2Cl_2$, $CHCl_3$, MeOH, $NH_4OH$ or mixtures thereof.

LC-MS-conditions 02 (if not indicated otherwise): Analytical: Thermo Finnigan MSQ Plus MS with Agilent 1100 Binary Pump and DAD. Column: Zorbax SB-AQ 5 μm, 4.6×50 mm ID from Agilent Technologies. Eluents: A: $H_2O$+0.04% TFA; B: $CH_3CN$; Gradient: 5% B→95% B over 1 min. Flow: 4.50 mL/min. Detection: UV/Vis and/or ELSD, and MS, $t_R$ is given in min.

LC-MS-conditions 07 (if not indicated otherwise): Analytical. Pump: Dionex HPG-3200RS, MS: Thermo MSQ Plus, DAD: Dionex DAD-3000RS, ELSD: Sedere Sedex 85. Column: Xbridge C18 2.5 μM, 4.6×30 mm ID from Waters, thermostated in the Dionex TCC-3200 compartment. Eluents: A: $H_2O$+0.04% TFA; B: $CH_3CN$. Method: Gradient: 5% B→95% B over 1.00 min. Flow: 4.5 mL/min. Detection: UV/Vis and/or ELSD, and MS, $t_R$ is given in min.

LC-MS-conditions 08 (if not indicated otherwise): Analytical. Pump: Dionex HPG-3200RS, MS: Thermo MSQ Plus, DAD: Dionex DAD-3000RS, ELSD: Sedere Sedex 85. Column: Zorbax SB-AQ 3.5 μm, 4.6×50 mm ID from Agilent Technologies, thermostated in the Dionex TCC-3200 compartment. Eluents: A: $H_2O$+0.04% TFA; B: $CH_3CN$. Method: Gradient: 5% B→95% B over 1.00 min. Flow: 4.5 mL/min. Detection: UV/Vis and/or ELSD, and MS, $t_R$ is given in min.

LC-MS-conditions 09 (if not indicated otherwise): Analytical. Pump: Agilent G1312A, MS: Thermo MSQ Plus, DAD: Agilent G1315A, ELSD: Sedere Sedex 85. Column: Waters XBridge C18 5 μm, 4.6×50 mm, Eluents: A: water/$NH_3$ [$c(NH_3)$=13 mmol/L]; B: $CH_3CN$; Eluent MakeUp: Buffer, $c(NH_4HCOO)$=10 mmol/L. Method: Gradient: 5% B→95% B over 0.75 min. Flow: 4.5 mL/min. Detection: UV/Vis and/or ELSD, and MS, $t_R$ is given in min.

LC-MS-conditions 10 (if not indicated otherwise): Analytical. Pump: Agilent_G4220A_, MS: Thermo MSQ Plus, DAD: Agilent_G4212A_, ELSD: Sedere Sedex 90. Column: Zorbax SB-AQ 3.5 μm, 4.6×50 mm ID from Agilent Technologies, thermostated in the Dionex TCC-3200 compartment. Eluents: A: H₂O+0.04% TFA; B: CH₃CN. Eluent MakeUp: CH₃CN/H₂O 7:3 at 0.250 mL/min. Method: Gradient: 5% B→95% B over 1.07 min. Flow: 4.5 mL/min. Detection: UV/Vis and/or ELSD, and MS, $t_R$ is given in min.

HPLC preparative: X-Bridge C18 5 μm, 50×19 mm ID from Waters. Eluents: A: H₂O+0.5% NH₄OH; B: CH₃CN; Gradient: 10% B→90% B over 5 min. Flow: 40.0 mL/min. Detection: UV/Vis and/or ELSD, and MS, $t_R$ is given in min.

HPLC chiral, analytical: (R,R) Whelk-O1 250×4.6 mm ID, 5 μm. Eluent A (80%): Heptane+0.05% DEA. Eluent B (20%): Ethanol+0.05% DEA. Flow: 0.8 mL/min. Detection: UV/Vis, $t_R$ is given in min.

NMR: Bruker Avance 400 (400 MHz); Varian Mercury 300 (300 MHz); chemical shifts are given in ppm relative to the solvent used; multiplicities: s=singlet, d=doublet, t=triplet, q=quadruplet, p=pentuplet, hex=hextet, hept=heptet, m=multiplet, br=broad, coupling constants are given in Hz.

The following examples illustrate the invention but do not at all limit the scope thereof.

General Procedure A: Amide Coupling:

In a flame dried round-bottomed flask equipped with a magnetic stir bar and under inert atmosphere (N₂), to a solution of the carboxylic acid (1.0 eq.) in CH₂Cl₂ (0.2 M) were added an amine (1.0-2.0 eq.), EDC HCl (2.0-4.0 eq.), HOBt (1.2-2.4 eq.) and DIPEA (3.0-6.0 eq.). The reaction mixture was stirred at rt until completion of the reaction. Water was then added, the layers separated and the org. layer dried over MgSO₄, filtered, and concentrated under reduced pressure. Purification of the residue, when necessary, by FC or HPLC gave the desired compound.

General Procedure B: Boc Deprotection

In a glass vial, under inert atmosphere (N₂), a solution of the Boc-protected amine (1.0 eq.) in CH₂Cl₂ was treated with 4N HCl in dioxane (10.0 eq.) and the reaction mixture was stirred at 0° C. or rt until completion of the reaction. The mixture was basified with 1M aq. NaOH and the compound was extracted with EA. The organic extracts were dried over MgSO₄, filtered, and concentrated under reduced pressure. The residue was purified, when necessary, by FC or HPLC to give the desired compound.

Synthesis of Intermediates

Spiro[2.4]hepta-4,6-diene

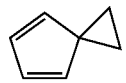

In a flame dried round-bottomed flask equipped with a magnetic stir bar and under inert atmosphere (N₂), a mixture of benzyltriethylammonium chloride (18.0 g, 78 mmol) in 50% aqueous NaOH solution (1.2 L) was heated to 45° C. A chilled solution of cyclopentadiene (formed by cracking of cyclopentadiene dimer at 180° C., 140 mL, 1.70 mol) in 1,2-dichloroethane (122 mL, 1.55 mol) was added to the stirred NaOH solution while keeping the internal temperature below 55° C. After completion of the addition (ca. 1.75 h), the reaction mixture was stirred at 50° C. for 2 h and allowed to cool down to rt. The layers were separated, the organic layer washed with 1M NaOH, dried (Na₂SO₄) and filtered. The crude brown liquid was distilled under reduced pressure (85-95 mbar) and the title compound was obtained as a colorless liquid (bp=45-50° C. at 80 mbar). ¹H NMR (400 MHz, CDCl₃) δ 6.58 (m, 2H), 6.19 (m, 2H), 1.71 (s, 4H).

Diels Alder reaction—formation of (5R,6R)-5,6-bis-[(1-(1S)-ethoxycarbonyl)-ethoxy-carbonyl]-(4S,7R)-[4,7-ethenylene-spiro[2.4]heptane]

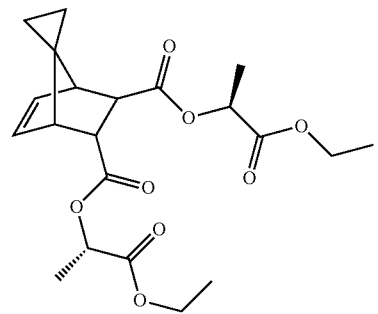 [SMILES: CCOC(=O)[C@H](C)OC(=O)C1C(C(=O)O[C@@H](C)C(=O)OCC)C2C=CC1C21CC1]

In a flame dried round-bottomed flask equipped with a magnetic stir bar and under inert atmosphere (N₂), to a solution of (E)-1,2-bis-[((1S)-1-ethoxycarbonyl)-ethoxy-carbonyl]-ethene (7.40 g, 22.7 mmol) in n-hexane (76 mL) was added spiro[2.4]hepta-4,6-diene (3.14 g, 34.0 mmol) at rt. The reaction mixture was stirred at this temperature overnight. The mixture was concentrated under reduced pressure and the crude residue purified by FC (hept/EA, 9:1). The title compound was obtained as a pale yellow oil. TLC: rf (hept/EA, 9:1)=0.25. LC-MS-conditions 02: $t_R$=1.12 min; [M+H]⁺= 409.00. ¹H NMR (400 MHz, CDCl₃) δ 6.44 (dd, J=5.5, 3.0 Hz, 1H), 6.32 (dd, J=5.5, 2.8 Hz, 1H), 5.12 (q, J=7.1 Hz, 1H), 5.06 (q, J=7.1 Hz, 1H), 4.28-4.14 (m, 4H), 3.76 (app. t, J=4.0 Hz, 1H), 2.92 (d, J=4.8 Hz, 1H), 2.86 (m, 1H), 2.80 (m, 1H), 1.55-1.47 (m, 6H), 1.29 (t, J=7.3 Hz, 3H), 1.29 (t, J=7.3 Hz, 3H), 0.70 (m, 1H), 0.56-0.44 (m, 3H).

Saponification—formation of (4S,7R)-[4,7-ethenylene-spiro[2.4]heptane]-(5R,6R)-5,6-bis-carboxylic acid

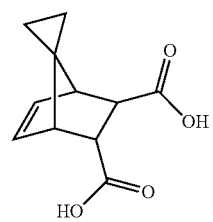 [SMILES: O=C(O)C1C(C(=O)O)C2C=CC1C21CC1]

To a solution of (5R,6R)-5,6-bis-[(1-(1S)-ethoxycarbonyl)-ethoxy-carbonyl]-(4S,7R)-[4,7-ethenylene-spiro[2.4]heptane] (9.51 g, 23.28 mmol) in THF/H₂O (1:1, 232 mL) was added LiOH (3.91 g, 93.13 mmol). The reaction mixture was stirred at rt overnight. 1N HCl was added in order to adjust the pH of the reaction mixture to pH=3, the layers separated and the aq. layer extracted with EA (3×). The combined org. extracts were dried over MgSO₄, filtered, and concentrated under reduced pressure. The crude residue was purified by FC (CH₂Cl₂/MeOH, 9:1) to give the title compound as a colorless oil. TLC: rf (CH$_2$Cl$_2$/MeOH, 9:1)=0.31. LC-MS-conditions 02: t$_R$=0.72 min; [M+CH$_3$CN+H]$^+$= 250.18.

Iodolactonization—formation of 6-iodo-2-oxo-hexahydrospiro[3,5-methanocyclopenta[b]furan-4,1'-cyclopropane]-7-carboxylic acid

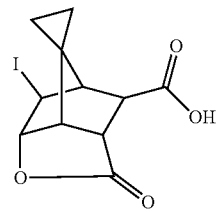 [SMILES: O=C(O)C1C2C(=O)OC3C(I)C1C1(CC1)C32]

To a solution of (4S,7R)-[4,7-ethenylene-spiro[2.4]heptane]-(5R,6R)-5,6-bis-carboxylic acid (5.60 g, 22.32 mmol) in CH$_2$Cl$_2$ (33 mL) were added NaHCO$_3$ (2.06 g, 24.56 mmol), water (100 mL), KI (1.37 g, 82.60 mmol) and I$_2$ (6.80 g, 26.79 mmol). The reaction mixture was stirred at rt for 3 h. The reaction was quenched by the addition of sat. aq. Na$_2$S$_2$O$_3$. The layers were separated and the aq. layer extracted with CH$_2$Cl$_2$ (3×). The combined org. extracts were dried over MgSO$_4$, filtered, and concentrated under reduced pressure. The crude foam was purified by FC (EA) to give the title compound as a white solid. TLC: rf (EA)=0.33.

Esterification—formation of methyl 6-iodo-2-oxo-hexahydrospiro[3,5-methanocyclopenta[b]furan-4,1'-cyclopropane]-7-carboxylate

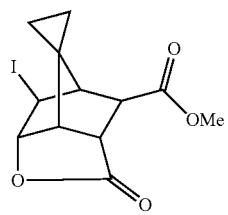 [SMILES: COC(=O)C1C2C(=O)OC3C(I)C1C1(CC1)C32]

In a flame dried round-bottomed flask equipped with a magnetic stir bar and under inert atmosphere (N$_2$), to a solution of 6-iodo-2-oxohexahydrospiro[3,5-methanocyclopenta[b]furan-4,1-cyclopropane]-7-carboxylic acid (5.00 g, 14.96 mmol) in dry MeOH (75 mL) was added TMSCH$_2$N$_2$ (2.0 M in hexanes, 37.0 mL, 74.83 mmol). The reaction mixture was stirred at rt overnight, concentrated under reduced pressure and purified by FC (hept/EA, 4:1) to give the title compound as a white solid. TLC: rf (hept/EA, 4:1)=0.18.

Retro-iodolactonization—formation of (6R)-6-methoxycarbonyl-(4S,7R)-[4,7-ethenylene-spiro[2.4]heptane]-(5R)-5-carboxylic acid

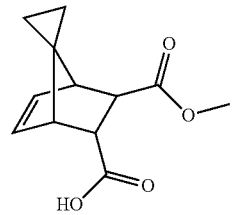 [SMILES: COC(=O)C1C(C(=O)O)C2C=CC1C21CC1]

In a flame dried round-bottomed flask equipped with a magnetic stir bar and under inert atmosphere (N$_2$), to a solution of methyl 6-iodo-2-oxohexahydrospiro[3,5-methanocyclopenta[b]furan-4,1'-cyclopropane]-7-carboxylate (2.86 g, 8.21 mmol) in acetic acid (29 mL) was added zinc powder (8.06 g, 123.23 mmol). The reaction mixture was stirred at 65° C. for 4 h, cooled down to rt, filtered and partitioned between water and EA. The layers were separated and the aq. layer extracted with EA (3×). The combined org. extracts were washed with brine, dried over MgSO$_4$, filtered, and concentrated under reduced pressure. The crude residue was purified by FC (hept/EA, 1:1) and the title compound was obtained as a colorless oil. TLC: rf (hept/EA, 1:1)=0.41.

Double bond reduction—formation of (6R)-6-methoxycarbonyl-(4S,7R)-[4,7-ethylene-spiro[2.4]heptane]-(5R)-5-carboxylic acid

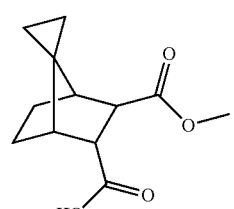

In a flame dried round-bottomed flask equipped with a magnetic stir bar and under inert atmosphere (N$_2$), a deoxygenated suspension of (6R)-6-methoxycarbonyl-(4S,7R)-[4,7-ethenylene-spiro[2.4]heptane]-(5R)-5-carboxylic acid (220 mg, 0.99 mmol), Pd/C 10% (44 mg) and cyclohexene (0.20 mL, 1.98 mmol) in dry THF (2.5 mL) was stirred at reflux for 2 h. The reaction mixture was filtered through celite and the filter cake washed with THF. The filtrate was concentrated under reduced pressure and the title compound obtained as a white solid. TLC: rf (hept/EA, 2:3)=0.48.

Amide coupling with 4-bromo-2-fluorobenzy-lamine—formation of (5R)—N$^5$-(4-bromo-2-fluorophenyl-methyl)-(6R)-6-methoxycarbonyl-(4S,7R)-[4,7-ethylene-spiro[2.4]heptane]-5-carboxamide

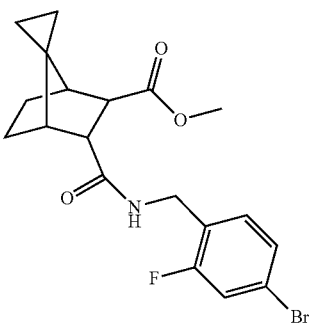 [SMILES: COC(=O)C1C(C(=O)NCc2ccc(Br)cc2F)C2CCC1C21CC1]

In a flame dried round-bottomed flask equipped with a magnetic stir bar and under inert atmosphere (N$_2$), to a solution of (6R)-6-methoxycarbonyl-(4S,7R)-[4,7-ethylene-spiro[2.4]heptane]-(5R)-5-carboxylic acid (5.00 g, 22.30 mmol) in dry CH$_2$Cl$_2$ (35 mL) were added 3 drops of DMF and oxalyl chloride (2.25 mL, 25.50 mmol). The reaction mixture was stirred at rt for 60 minutes and concentrated under reduced pressure. To a suspension of 4-bromo-2-fluorobenzylamine hydrochloride (5.42 g, 22.30 mmol) in pyridine (5.40 mL) was added a solution of the acyl chloride in acetone (35 mL). The reaction mixture was stirred at rt for 1 h, diluted with EA and successively washed with aq. 1N HCl, sat. aq. NaHCO$_3$ and brine. The org. layer was dried over MgSO$_4$, filtered, and concentrated under reduced pressure to give the title compound obtained as a yellow oil. LC-MS-conditions 08: $t_R$=0.94 min; [M+H]$^+$=409.84.

(5R)—N$^5$-(4-Bromo-2-fluorophenyl-methyl)-(6R)-6-hydroxycarbonyl-(4S,7R)-[4,7-ethylene-spiro[2.4]heptane]-5-carboxamide (WO2010/134014)

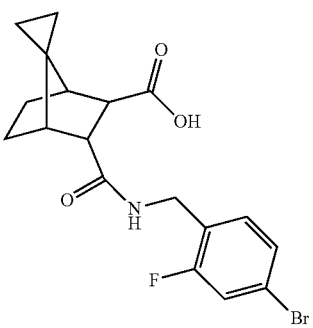 [SMILES: O=C(O)C1C(C(=O)NCc2ccc(Br)cc2F)C2CCC1C21CC1]

To a solution of (5R)—N$^5$-(4-bromo-2-fluorophenyl-methyl)-(6R)-6-methoxycarbonyl-(4S,7R)-[4,7-ethylene-spiro[2.4]heptane]-5-carboxamide (5.70 g, 13.90 mmol) in THF (100 mL) was added aq. 2N NaOH (31.00 mL, 62.00 mmol). The reaction mixture was stirred at rt until completion of the reaction. The mixture was then poured into aq. 1N HCl and extracted with EA (3×). The combined org. extracts were washed with brine, dried over MgSO$_4$, filtered, and concentrated under reduced pressure to give the title compound as a white foam. LC-MS-conditions 08: $t_R$=0.85 min; [M+H]$^+$=395.77.

1-Benzyl-3,3-difluoropiperidin-4-ol

In a flame dried round-bottomed flask equipped with a magnetic stir bar and under inert atmosphere (N$_2$), to a solution of 1-benzyl-3,3-difluoropiperidine-4,4-diol (WO2008/121687 and WO2005/040120) (2.88 g, 11.85 mmol) in dry MeOH (58 mL) was added NaBH$_4$ (672 mg, 17.76 mmol) portionwise at 0° C. The reaction mixture was stirred at 0° C. for 15 min. Aq. 0.1M NaHCO$_3$ (5 mL) was then added and the mixture further stirred for 5 min, dried (MgSO$_4$), filtered and concentrated under reduced pressure. The crude residue was purified by FC (hept/EA, 2:1→1:1) and the title compound obtained as a beige oil. LC-MS-conditions 08: $t_R$=0.42 min; [M+H]$^+$=228.32.

3,3-Difluoropiperidin-4-ol

In a flame dried round-bottomed flask equipped with a magnetic stir bar, a suspension of 1-benzyl-3,3-difluoropiperidin-4-ol (1.73 g, 7.62 mmol) and Pd(OH)$_2$ (20% Pd, 107 mg) in dry EtOH (50 mL) was stirred at rt under a H$_2$ atmospheric pressure until completion of the reaction. The mixture was then filtered, washed with EA/EtOH, and the filtrate concentrated under reduced pressure to give the title compound as a beige solid. LC-MS-conditions 08: $t_R$=0.15 min; [M+H]$^+$=138.27.

tert-Butyl 3,3-difluoro-4-hydroxypiperidine-1-carboxylate

In a flame dried round-bottomed flask equipped with a magnetic stir bar and under inert atmosphere (N$_2$), to a solution of 3,3-difluoropiperidin-4-ol (700 mg, 5.10 mmol) in dry CH$_2$Cl$_2$ (50 mL) was added Boc$_2$O (1.11 g, 5.10 mmol). The reaction mixture was stirred at rt for 2 h. Water was then added, the layers separated and the aq. layer extracted with CH$_2$Cl$_2$ (3×). The combined org. extracts were washed with brine, dried over MgSO$_4$, filtered, and concentrated under reduced pressure to give the title compound as a yellow solid. LC-MS-conditions 08: $t_R$=0.69 min; [M-CH$_3$+H]$^+$=223.30.

tert-Butyl 4-(benzylamino)-3,3-difluoropiperidine-1-carboxylate

In a flame dried round-bottomed flask equipped with a magnetic stir bar and under inert atmosphere (N$_2$), to an ice-cold solution of tert-butyl 3,3-difluoro-4-hydroxypiperidine-1-carboxylate (2.40 g, 10.00 mmol) in dry CH$_2$Cl$_2$ (50 mL) was added a solution of Dess-Martin periodinane (50 mL of a 15% solution in CH$_2$Cl$_2$, 24.00 mmol). The reaction mixture was stirred at rt until completion of the reaction. Sat. aq. NaHCO$_3$ (50 mL) was then added followed by 10% aq. Na$_2$SO$_3$ (50 mL). The mixture was stirred at rt for 1 h, the layers separated and the aq. layer extracted with CH$_2$Cl$_2$ (3×). The combined org. extracts were dried over MgSO$_4$, filtered, and concentrated under reduced pressure. The crude residue was redissolved in CH$_2$Cl$_2$ (30 mL) and stirred in the presence of molecular sieves for 24 h, filtered, and concentrated under reduced pressure to give tert-butyl 3,3-difluoro-4-oxopiperidine-1-carboxylate as a yellow solid.

To a solution of tert-butyl 3,3-difluoro-4-oxopiperidine-1-carboxylate (0.250 g, 1.06 mmol) in CH$_2$Cl$_2$ (4.5 mL) was added benzylamine (0.13 mL, 1.17 mmol) and sodium triacetoxyborohydride (0.356 g, 1.59 mmol) and the solution was stirred at rt for 22 h. The reaction mixture was treated with sat. aq. $Na_2CO_3$ and extracted with EA (3×50 mL). The combined organic extracts were dried over MgSO4, filtered, and the solvent removed under reduced pressure. The residue was purified by FC (Heptane/EA, 1:1) to give tert-butyl 4-(benzylamino)-3,3-difluoropiperidine-1-carboxylate. LC-MS-conditions 08: $t_R$=0.65 min; $[M+H]^+$=327.32.

tert-Butyl
4-amino-3,3-difluoropiperidine-1-carboxylate

In a flame dried round-bottomed flask equipped with a magnetic stir bar and under inert atmosphere ($N_2$), tert-butyl 4-(benzylamino)-3,3-difluoropiperidine-1-carboxylate (0.186 g, 0.57 mmol) was dissolved in MeOH (5 mL) and wet Pd/C 10% (50 mg) was added. The flask was purged with $H_2$ gas and the reaction mixture stirred under an $H_2$ atmosphere for 2 h at rt. The reaction mixture was filtered over celite and the cake was washed with MeOH and EA. The filtrate was concentrated under reduced pressure to give tert-butyl 4-amino-3,3-difluoropiperidine-1-carboxylate as a colorless oil. LC-MS-conditions 08: $t_R$=0.49 min; $[M-CH_3+H]^+$=222.32.

tert-Butyl 3-fluoro-4-oxopiperidine-1-carboxylate

In a flame dried round-bottomed flask equipped with a magnetic stir bar and under inert atmosphere ($N_2$), to a solution of tert-butyl 4-oxopiperidine-1-carboxylate (5.00 g, 25.09 mmol) in dry DMF (25 mL) was added trimethylsilyl chloride (5.77 mL, 45.17 mmol) followed by $Et_3N$ (8.38 mL, 60.23 mmol) at rt. The reaction mixture was stirred at 80° C. for 24 h. The mixture was then cooled to rt, diluted with hexanes and washed with sat. aq. $NaHCO_3$. The layers were separated and the org. layer dried over $MgSO_4$, filtered, and concentrated under reduced pressure. The residue was purified by FC (hexanes/EA, 9:1) to afford tert-butyl 4-((trimethylsilyl)oxy)-5,6-dihydropyridine-1(2H)-carboxylate as a colorless oil. Rf (Hexanes/EA, 9:1)=0.50.

In a flame dried round-bottomed flask equipped with a magnetic stir bar and under inert atmosphere ($N_2$), to a solution of tert-butyl 4-((trimethylsilyl)oxy)-5,6-dihydropyridine-1(2H)-carboxylate (5.00 g, 18.40 mmol) in dry acetonitrile (25 mL) was added Selectfluor® (7.55 g, 20.3 mmol) at rt. The reaction mixture was stirred at rt for 2 h then poured into EA and successively washed with aq. 1% $NaHCO_3$ and brine. The org. layer was dried over $MgSO_4$, filtered, and concentrated under reduced pressure. The residue was purified by FC (hexanes/EA, 4:1) to afford the title compound as a pale yellow solid. LC-MS-conditions 08: $t_R$=0.55 min; $[M-CH_3+H]^+$=203.23; TLC: rf (hexanes/EA, 4:1)=0.17.

trans-tert-Butyl 4-amino-3-fluoropiperidine-1-carboxylate and cis-tert-butyl 4-amino-3-fluoropiperidine-1-carboxylate In a flame dried round-bottomed flask equipped with a magnetic stir bar and under inert atmosphere ($N_2$), to a solution of tert-butyl 3-fluoro-4-oxopiperidine-1-carboxylate (0.80 g, 3.68 mmol) in MeOH (10 mL) was added ammonium acetate (1.99 g, 25.80 mmol) and the resulting solution stirred at rt for 2 h. $NaCNBH_3$ (0.29 g, 4.42 mmol) was then added and the solution stirred at rt overnight. The reaction mixture was concentrated to dryness and the organics extracted with EA from a 1% aq. solution of $Na_2CO_3$. The combined organic extracts were washed with brine, dried over $MgSO_4$, filtered and concentrated under reduced pressure. The residue was purified with FC ($CH_2Cl_2$/MeOH, 9:1) to afford trans-tert-butyl 4-amino-3-fluoropiperidine-1-carboxylate and cis-tert-butyl 4-amino-3-fluoropiperidine-1-carboxylate both as colorless oils which solidified upon standing. LC-MS-conditions 08: $t_R$=0.48 min; $[M-CH_3+H]^+$=204.25 and $t_R$=0.46; $[M+H]^+$=219.26; TLC: rf ($CH_2Cl_2$/MeOH, 9:1)=0.30 and 0.09.

trans-tert-Butyl
3-azido-4-fluoropyrrolidine-1-carboxylate

In a flame dried round-bottomed flask equipped with a magnetic stir bar and under inert atmosphere ($N_2$), to a solution of trans-tert-butyl 3-azido-4-hydroxypyrrolidine-1-carboxylate (*J. Med. Chem.* 2010, 53, 6730-6746) (288 mg, 1.26 mmol) in $CH_2Cl_2$ (1.1 mL) was added dropwise a solution of DAST (0.345 mL, 2.61 mmol) in $CH_2Cl_2$ (1.1 mL) at −78° C. After being stirred for 2 h at −60° C., the reaction mixture was warmed to 0° C., poured into aq. 10% $Na_2CO_3$, and extracted with $CH_2Cl_2$. The organic layer was separated, washed with water, dried over $MgSO_4$, and concentrated under reduced pressure. The residue was purified with FC (Hept/EA, 9.5:0.5→7:3) to afford trans-tert-butyl 3-azido-4-fluoropyrrolidine-1-carboxylate as a yellow oil. TLC: rf (Hept/EA, 7:3)=0.53.

trans-tert-Butyl
3-amino-4-fluoropyrrolidine-1-carboxylate

In a round-bottomed flask equipped with a magnetic stir bar and a reflux condenser, to a solution of trans-tert-butyl 3-azido-4-fluoropyrrolidine-1-carboxylate (45 mg, 0.195 mmol) in THF (2.5 mL) was added $PPh_3$ on polystyrene (1.6 mmol/g, 120 mg, 0.193 mmol) and water (0.15 mL). The reaction mixture was stirred at 60° C. for 2 h. The mixture was then filtered and the filtrate dried over $MgSO_4$ and filtered. The solvent was removed under reduced pressure to afford trans-tert-butyl 3-amino-4-fluoropyrrolidine-1-carboxylate as a pale yellow oil. LC-MS-conditions 10: $t_R$=0.48 min; $[M-CH_3+H]^+$=190.38.

trans-tert-Butyl
3-azido-4-(tosyloxy)pyrrolidine-1-carboxylate

In a flame dried round-bottomed flask equipped with a magnetic stir bar and under inert atmosphere ($N_2$), to a solution of trans-tert-butyl 3-azido-4-hydroxypyrrolidine-1-carboxylate (*J. Med. Chem.* 2010, 53, 6730-6746) (320 mg, 1.40 mmol) in pyridine (3 mL) was added TsCl (588 mg, 3.00 mmol). The mixture was stirred at 5° C. overnight. The solvent was removed under reduced pressure and the mixture was partitioned between $CH_2Cl_2$ and 10% aq. $NaHCO_3$. The organic layer was washed with water, dried over $MgSO_4$, and the solvent removed under reduced pressure. The residue was purified by FC (Hept/EA, 9.5:0.5→8:2) to afford trans-tert-butyl 3-azido-4-(tosyloxy)pyrrolidine-1-carboxylate as a colorless oil. LC-MS-conditions 08: $t_R$=0.96 min; $[M-CH_3+H]^+$=368.10. TLC: rf (Hept/EA, 8:2)=0.22.

cis-tert-Butyl
3-azido-4-fluoropyrrolidine-1-carboxylate

In a flame dried round-bottomed flask equipped with a magnetic stir bar, a reflux condenser, and under inert atmosphere ($N_2$), a solution of trans-tert-butyl 3-azido-4-(tosyloxy)pyrrolidine-1-carboxylate (438 mg, 1.15 mmol) in 1M tetra-n-butyl-ammonium fluoride solution in THF (7.00 mL, 7.00 mmol) was stirred at reflux overnight. The reaction mixture was concentrated under reduced pressure and the residue was extracted with $CH_2Cl_2$, washed with water, dried over $MgSO_4$, filtered, and concentrated under reduced pressure. The residue was purified by FC (Hept/EA, 9:1→7:3) to afford cis-tert-butyl 3-azido-4-fluoropyrrolidine-1-carboxylate as a colorless oil. TLC: rf (Hept/EA, 7:3)=0.33. LC-MS-conditions 08: $t_R$=0.81 min; $[M-CH_3+H]^+$=216.15.

cis-tert-Butyl 3-amino-4-fluoropyrrolidine-1-carboxylate

In a round-bottomed flask equipped with a magnetic stir bar and a reflux condenser, to a solution of cis-tert-butyl 3-azido-4-fluoropyrrolidine-1-carboxylate (86 mg, 0.374 mmol) in THF (5.5 mL) was added $PPh_3$ on polystyrene (1.6 mmol/g, 280 mg, 0.448 mmol) and water (0.33 mL). The reaction mixture was stirred at 60° C. for 2 h. The mixture was then filtered and the filtrate dried over $MgSO_4$ and filtered. The solvent was removed under reduced pressure to afford cis-tert-butyl 3-amino-4-fluoropyrrolidine-1-carboxylate as a colorless oil. LC-MS-conditions 10: $t_R$=0.45 min; $[M-CH_3+H]^+$=190.41.

tert-Butyl 4-((1S,2R,3R,4R)-2-(4-bromo-2-fluorobenzyl)carbamoyl)spiro[bicyclo[2.2.1]heptane-7,1'-cyclopropan]-3-ylcarboxamido)-3,4-trans-fluoro piperidine-1-carboxylate

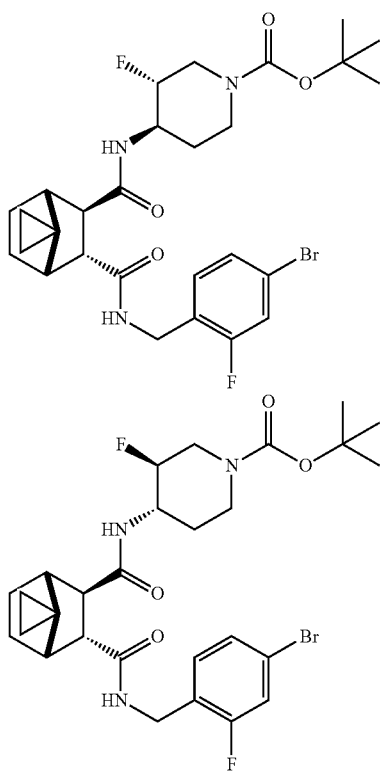

Following general procedure A starting from (5R)—$N^5$-(4-bromo-2-fluorophenyl-methyl)-(6R)-6-hydroxycarbonyl-(4S,7R)-[4,7-ethylene-spiro[2.4]heptane]-5-carboxamide and racemic trans-tert-butyl 4-amino-3-fluoropiperidine-1-carboxylate. The diastereomers were separated by FC (hept/EA, 1:0 to 6:4). First eluting diastereomer: LC-MS-conditions 08: $t_R$=0.98 min; $[M+H]^+$=596.26; TLC: rf (Hept/EA, 6:4)=0.22. Second eluting diastereomer: $t_R$=0.97 min; $[M+H]^+$=596.25; TLC: rf (Hept/EA, 6:4)=0.13.

PREPARATION OF EXAMPLES

Example 1

(1S,2R,3R,4R)—$N^2$-(4-Bromo-2-fluorobenzyl)-$N^3$-(3,3-difluoropiperidin-4-yl)spiro[bicyclo[2.2.1]heptane-7,1'-cyclopropane]-2,3-dicarboxamide Following general procedures A and B, starting from (5R)—$N^5$-(4-bromo-2-fluorophenyl-methyl)-(6R)-6-hydroxycarbonyl-(4S,7R)-[4,7-ethylene-spiro[2.4]heptane]-5-carboxamide and racemic tert-butyl 4-amino-3,3-difluoropiperidine-1-carboxylate.

LC-MS-conditions 08: $t_R$=0.71 min; $[M+H]^+$=514.26.

Example 2

(1S,2R,3R,4R)—$N^2$-(4-Bromo-2-fluorobenzyl)-$N^3$-(trans-3-fluoropiperidin-4-yl)spiro[bicyclo[2.2.1]heptane-7,1'-cyclopropane]-2,3-dicarboxamide (diastereoisomer 1)

Following general procedure B starting from the first eluting diastereoisomer tert-butyl 4-((1S,2R,3R,4R)-2-((4-bromo-2-fluorobenzyl)carbamoyl)spiro[bicyclo[2.2.1]heptane-7,1'-cyclopropan]-3-ylcarboxamido)-3,4-trans-fluoro piperidine-1-carboxylate. LC-MS-conditions 08: $t_R$=0.70 min; $[M+H]^+$=496.24. HPLC chiral, analytical: $t_R$=12.72 min.

Example 3

(1S,2R,3R,4R)—$N^2$-(4-Bromo-2-fluorobenzyl)-$N^3$-(trans-3-fluoropiperidin-4-yl)spiro[bicyclo[2.2.1]heptane-7,1'-cyclopropane]-2,3-dicarboxamide (diastereoisomer 2)

Following general procedure B starting from the second eluting diastereoisomer tert-butyl 4-((1S,2R,3R,4R)-2-((4-bromo-2-fluorobenzyl)carbamoyl)spiro[bicyclo[2.2.1]heptane-7,1'-cyclopropan]-3-ylcarboxamido)-3,4-trans-fluoro piperidine-1-carboxylate. LC-MS-conditions 08: $t_R$=0.69 min; $[M+H]^+$=496.27. HPLC chiral, analytical: $t_R$=10.58 min.

Example 4

(1S,2R,3R,4R)—$N^2$-(4-Bromo-2-fluorobenzyl)-$N^3$-(cis-3-fluoropiperidin-4-yl)spiro[bicyclo[2.2.1]heptane-7,1'-cyclopropane]-2,3-dicarboxamide Following general procedures A and B starting from (5R)—$N^5$-(4-bromo-2-fluorophenyl-methyl)-(6R)-6-hydroxycarbonyl-(4S,7R)-[4,7-ethylene-spiro[2.4]heptane]-5-carboxamide and cis-tert-butyl 4-amino-3-fluoropiperidine-1-carboxylate to afford (1S,2R,3R,4R)—$N^2$-(4-bromo-2-fluorobenzyl)-$N^3$-(cis-3-fluoropiperidin-4-yl)spiro[bicyclo

[2.2.1]heptane-7,1'-cyclopropane]-2,3-dicarboxamide as a mixture of diastereoisomers. LC-MS-conditions 09: $t_R$=0.82 min; [M+H]$^+$=495.98.

Example 5

(1S,2R,3R,4R)—N$^2$-(4-Bromo-2-fluorobenzyl)-N$^3$-(cis-4-fluoropyrrolidin-3-yl)spiro[bicyclo[2.2.1]heptane-7,1'-cyclopropane]-2,3-dicarboxamide Following general procedures A and B starting from (5R)—N$^5$-(4-bromo-2-fluorophenyl-methyl)-(6R)-6-hydroxycarbonyl-(4S,7R)-[4,7-ethylene-spiro[2.4]heptane]-5-carboxamide and cis-tert-butyl 3-amino-4-fluoropyrrolidine-1-carboxylate to afford (1S,2R,3R,4R)—N$^2$-(4-bromo-2-fluorobenzyl)-N$^3$-(cis-4-fluoropyrrolidin-3-yl)spiro[bicyclo[2.2.1]heptane-7,1'-cyclopropane]-2,3-dicarboxamide as a mixture of diastereoisomers. LC-MS-conditions 10: $t_R$=0.70 min; [M+H]$^+$=482.12.

Example 6

(1S,2R,3R,4R)—N$^2$-(4-Bromo-2-fluorobenzyl)-N$^3$-(trans-4-fluoropyrrolidin-3-yl)spiro[bicyclo[2.2.1]heptane-7,1'-cyclopropane]-2,3-dicarboxamide Following general procedures A and B starting from (5R)—N$^5$-(4-bromo-2-fluorophenyl-methyl)-(6R)-6-hydroxycarbonyl-(4S,7R)-[4,7-ethylene-spiro[2.4]heptane]-5-carboxamide and trans-tert-butyl 3-amino-4-fluoropyrrolidine-1-carboxylate to afford (1S,2R,3R,4R)—N$^2$-(4-bromo-2-fluorobenzyl)-N$^3$-(trans-4-fluoropyrrolidin-3-yl)spiro[bicyclo[2.2.1]heptane-7,1-cyclopropane]-2,3-dicarboxamide as a mixture of diastereoisomers. LC-MS-conditions 10: $t_R$=0.70 min; [M+H]$^+$=482.12.

PREPARATION OF REFERENCE EXAMPLES tert-Butyl 4-((1S,2R,3R,4R)-2-((4-bromo-2-fluorobenzyl)carbamoyl)spiro[bicyclo[2.2.1]heptane-7,1'-cyclopropan]-3-ylcarboxamido)piperidine-1-carboxylate Following general procedure A starting from (5R)—N$^5$-(4-bromo-2-fluorophenyl-methyl)-(6R)-6-hydroxycarbonyl-(4S,7R)-[4,7-ethylene-spiro[2.4]heptane]-5-carboxamide and tert-butyl 4-aminopiperidine-1-carboxylate. The residue was purified by FC (CH$_2$Cl$_2$/MeOH/NH$_4$OH, 98:2:0.5) to afford tert-butyl 4-((1S,2R,3R,4R)-2-((4-bromo-2-fluorobenzyl)carbamoyl)spiro[bicyclo[2.2.1]heptane-7,1'-cyclopropan]-3-ylcarboxamido) piperidine-1-carboxylate. LC-MS-conditions 07: $t_R$=0.93 min; [M+H]$^+$=577.55.

Reference Example 1

(1S,2R,3R,4R)—N$^2$-(4-Bromo-2-fluorobenzyl)-N$^3$-(piperidin-4-yl)spiro[bicyclo[2.2.1]heptane-7,1'-cyclopropane]-2,3-dicarboxamide hydrochloride In a glass vial, under inert atmosphere (N$_2$), a solution of tert-butyl 4-((1S,2R,3R,4R)-2-((4-bromo-2-fluorobenzyl) carbamoyl)spiro[bicyclo[2.2.1]heptane-7,1'-cyclopropan]-3-ylcarboxamido)piperidine-1-carboxylate (1.0 eq.) in CH$_2$Cl$_2$ was treated with 4N HCl in dioxane (10.0 eq.) and the reaction mixture was stirred at 0° C. or rt until completion of the reaction. The reaction mixture was then concentrated under reduced pressure to afford 4-((1S,2R,3R,4R)-2-((4-bromo-2-fluorobenzyl)carbamoyl)spiro[bicyclo[2.2.1]heptane-7,1'-cyclopropan]-3-ylcarboxamido)piperidin-1-ium chloride. LC-MS-conditions 07: $t_R$=0.65 min; [M+H]$^+$=477.97.

Reference Example 2

(1S,2R,3R,4R)—N$^2$-(4-Bromo-2-fluorobenzyl)-N$^3$-(piperidin-4-yl)spiro[bicyclo[2.2.1]heptane-7,1'-cyclopropane]-2,3-dicarboxamide Following general procedures A and B starting from (5R)—N$^5$-(4-bromo-2-fluorophenyl-methyl)-(6R)-6-hydroxycarbonyl-(4S,7R)-[4,7-ethylene-spiro[2.4]heptane]-5-carboxamide and tert-butyl 4-aminopiperidine-1-carboxylate to afford (1S,2R,3R,4R)—N$^2$-(4-bromo-2-fluorobenzyl)-N$^3$-(piperidin-4-yl)spiro[bicyclo[2.2.1]heptane-7,1'-cyclopropane]-2,3-dicarboxamide. LC-MS-conditions 03: $t_R$=1.12 min; [M+H]$^+$=478.04.

II. Biological Assays

In Vitro Assay

The ALX receptor agonistic activities of the compounds of formula (I) are determined in accordance with the following experimental method.

Experimental Method

Intracellular Calcium Measurements

Cells expressing recombinant human ALX receptor and the G-protein Gα16 (HEK293-hALXR-Gα16) were grown to 80% confluency in Growing Medium (GM). Cells were detached from culture dishes with a cell dissociation buffer (Invitrogen, 13151-014), and collected by centrifugation at 1'000 rpm at rt for 5 min in Assay Buffer (AB) (equal parts of Hank's BSS (Gibco, 14065-049) and DMEM without Phenol Red (Gibco, 11880-028)). After 60 min incubation at 37° C. under 5% CO$_2$ in AB supplemented with 1 µM Fluo-4 (AM) (Invitrogen, F14202) and 20 mM HEPES (Gibco, 15630-056), the cells were washed and resuspended in AB. They were then seeded onto 384-well FLIPR assay plates (Greiner, 781091) at 50'000 cells in 70 µl per well and sedimented by centrifugation at 1'000 rpm for 1 min. Stock solutions of test compounds were made up at a concentration of 10 mM in DMSO, and serially diluted in AB to concentrations required for activation dose response curves. WKYMVm (Phoenix Peptides) was used as a reference agonist. A FLIPR Tetra instrument (Molecular Devices) was operated according to the manufacturer's standard instructions, adding 4 µl of test compound dissolved at 10 mM in DMSO and diluted prior to the experiment in assay buffer to obtain the desired final concentration. Changes in fluorescence were monitored before and after the addition of test compounds at λex=488 nm and λem=540 nm. Emission peak values above base level after compounds addition were exported after base line subtraction. Values were normalized to high-level control (WKYMVm compound, 10 nM final concentration) after subtraction of the base line value (AB addition).

Agonistic activities with respect to the ALX receptor (EC$_{50}$ values) of exemplified compounds are displayed in Table 1.

TABLE 1

| Compound | EC$_{50}$ [nM] |
|---|---|
| Example 1: (1S,2R,3R,4R)-N$^2$-(4-bromo-2-fluorobenzyl)-N$^3$-(3,3-difluoropiperidin-4-yl)spiro[bicyclo[2.2.1]heptane-7,1'-cyclopropane]-2,3-dicarboxamide | 41 |
| Example 2: (1S,2R,3R,4R)-N$^2$-(4-bromo-2-fluorobenzyl)-N$^3$-(trans-3-fluoropiperidin-4-yl)spiro[bicyclo[2.2.1]heptane-7,1'-cyclopropane]-2,3-dicarboxamide (diastereoisomer 1) | 1.9 |
| Example 3: (1S,2R,3R,4R)-N$^2$-(4-bromo-2-fluorobenzyl)-N$^3$-(trans-3-fluoropiperidin-4-yl)spiro[bicyclo[2.2.1]heptane-7,1'-cyclopropane]-2,3-dicarboxamide (diastereoisomer 2) | 2.0 |
| Example 4: (1S,2R,3R,4R)-N$^2$-(4-bromo-2-fluorobenzyl)-N$^3$-(cis-3-fluoropiperidin-4-yl)spiro[bicyclo[2.2.1]heptane-7,1'-cyclopropane]-2,3-dicarboxamide | 12.7 |
| Example 5: (1S,2R,3R,4R)-N$^2$-(4-Bromo-2-fluorobenzyl)-N$^3$-(cis-4-fluoropyrrolidin-3-yl)spiro[bicyclo[2.2.1]heptane-7,1'-cyclopropane]-2,3-dicarboxamide | 300 |
| Example 6: (1S,2R,3R,4R)-N$^2$-(4-Bromo-2-fluorobenzyl)-N$^3$-(trans-4-fluoropyrrolidin-3-yl)spiro[bicyclo[2.2.1]heptane-7,1'-cyclopropane]-2,3-dicarboxamide | 4.5 |

Glutathione Addition Assay

To a solution of substrate (0.05 mmol) in 0.5 mL CH$_3$CN (0.5 mL) was added a solution of GSH (10.0-20.0 eq) in 0.5 mL phosphate buffer (0.1 M, pH 7.4). The resulting cloudy solution was stirred at 40° C. for 2 h and analyzed by LC-MS.

Dansyl-Glutathione Trapping Assay

In Vitro Incubation

Test compounds are generally preincubated at 10 µM in 0.1 M potassium phosphate buffer (pH 7.4) with 1 mg/mL human liver microsomes and 1 mM dansyl-GSH for 5 min at 37° C. in light protected tubes. The reaction is initiated by adding an NADPH-regenerating system. After 60 min, the reaction is stopped by the addition of two volumes of ice-cold methanol with 5 mM dithiothreitol (DTT). Following centrifugation, supernatants are further analysed by HPLC with fluorescence detection. Control experiments are done in the presence of GSH instead of dansyl-GSH in order to identify fluorescent parents and/or metabolites as interference. Another control is performed in the absence of parent drug to determine background signals due to degradation/impurities of dansyl-glutathione.

Analytics/Quantification

Supernatants of incubated samples are introduced into a Shimadzu HPLC system with fluorescence detector ($\lambda_{ex}$ 340, $\lambda_{em}$ 525 nm) capable to run with higher pressure (600 bar). The separation is accomplished using a 4.6×100 mm RP Kinetics column (Phenomenex, 2.6 µm) at 1.5 ml/min. A full gradient is used with water and acetonitrile both acidified with 0.1% formic acid. A volume of 2 ml acetonitrile is added post-column to reduce solvent dependant fluorescence. Dansyl-GSH trapped compounds are identified via visual comparison of chromatograms of incubations and control samples. The amount of trapped material is quantified by an external calibration with known concentrations of dansyl-GSH and expressed in nmol/l*h or pmol/ml*h.

Determination of Pharmacokinetic Parameters

The goal of the study was to evaluate the pharmacokinetics of compounds after a single oral administration or after an intravenous route in normal, conscious rats.

Method Description:

Anaesthesia: Wistar rats were pretreated with 0.03 mg/kg Buprenorphine s.c. (an analgesic-stock solution at 0.03 mg/ml) and 30 minutes later they were anaesthetized with a mixture of 90 mg/kg Ketamine and 10 mg/kg Xylazine i.p. or under Isoflurane inhalation anesthesia.

Rat preparation: The top of the head and the neck were shaved and disinfected with Merfen and Betadine.

Surgery: While under (isoflurane) anaesthesia, an incision was made above 1.5 cm at the top of the head (between the ears) in order to fix the anchor button. A second incision was made above 1.5-2 cm on the neck (near the right clavicle). A catheter (ID/DI: 0.508 mm, Ulrich Swiss) was tunnelled with a trocar under the skin and an access port was fixed with 4-0 silk. The catheter was then filled with a heparinized saline solution (100 Ul/ml), clamped with a hemostat to prevent loss of saline, and the wound was closed with tissue adhesive (3M Vetbond). Next, the jugular vein was isolated and ligated cranially with 4-0 silk, a second ligature, placed caudal to the first ligature, was not tightened. Using iridectomy scissors, a V-shaped hole was cut in the vein, and the catheter was gently pushed into the vessel. All ligatures were then tied around the vessel and the catheters. A NaCl-heparin 100 Ul flush was made to test the blood flow. The wound was then closed with tissue adhesive and a suture. Flush again.

Post operative care: After the operation each animal was housed separately in a small box with food (directly on the floor of the box) and water ad libitum and access to solid drink. One to two days were allowed for recovery from surgery prior to the experiment. The day following the operation, animals were flushed with NaCl-heparin 100 Ul/mL and blood collection tubes were prepared with 10 µl EDTA added to each tube.

Experiment: Tested compounds were given at 1 mg/kg orally and intravenously. The oral formulation was as a solution in Gelatine (98% of a 7.5% Gelatine solution in Water and 2% DMSO) and the intravenous formulation was a solution in water with pH adjustment or in cyclodextrine (5% DMSO, 95% HPBCD30% (w/v)). After application of the test-compound (p.o. or i.v.), blood samples (2500) were taken at different times. The samples were immediately put in ice before being centrifuged (4° C., 8 min, 16000 g). The plasma was then aspirated and placed into a 96 well plate. The plate was kept at −20° C. until analysis could be performed.

Plasma concentration of the compound was determined using a LC-MS/MS method.

TABLE 2 pharmacokinetic data
(AUC: area under curve after p.o. administration; F: bioavailability)

| compound | administration | AUC [ng · h/mL] | F[1] [%] |
|---|---|---|---|
| (1S,2R,3R,4R)-N$^2$-(4-bromo-2-fluorobenzyl)-N$^3$-(trans-3-fluoropiperidin-4-yl)spiro[bicyclo[2.2.1]heptane-7,1'-cyclopropane]-2,3-dicarboxamide (example 3) | p.o.: 1 mg/kg | 49.9 | 12 |
| (1S,2R,3R,4R)-N$^2$-(4-Bromo-2-fluorobenzyl)-N$^3$-(piperidin-4-yl)spiro[bicyclo[2.2.1]heptane-7,1'-cyclopropane]-2,3-dicarboxamide (reference example 2; compound falling within formula I of WO2010/134014) | p.o.: 1 mg/kg | 6.34 | 0.3 |

[1]F calculated with a reference AUC after iv administration of solutions at 1 mg/kg

The invention claimed is:

1. A compound of formula (I)

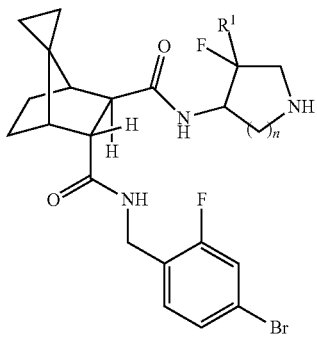

(I)

wherein
n represents 1 or 2; and
R$^1$ represents hydrogen or fluoro;
or a salt thereof.

2. The compound according to claim 1, wherein n represents 1; or a salt thereof.

3. The compound according to claim 1, wherein n represents 2; or a salt thereof.

4. The compound according to claim 1, wherein R$^1$ represents hydrogen; or a salt thereof.

5. The compound according to claim 1, wherein R$^1$ represents fluoro; or a salt thereof.

6. The compound according to claim 1, wherein R$^1$ represents hydrogen and the two stereogenic centers at the heterocyclyl group, which is attached to the amide nitrogen-atom, are relative to each other in trans-configuration;
or a salt thereof.

7. The compound according to claim 1, wherein said compound is:
(1S,2R,3R,4S)-N2-(4-bromo-2-fluorobenzyl)-N3 S,4S)-3-fluoropiperidin-4-yl)spiro[bicyclo[2.2.1]heptane-7,1'-cyclopropane]-2,3-dicarboxamide;
(1 S,2R,3R,4R)—N2-(4-bromo-2-fluorobenzyl)-N3-((3R,4R)-3-fluoropiperidin-4-yl)spiro[bicyclo[2.2.1]heptane-7,1'-cyclopropane]-2,3-dicarboxamide;
(1S,2R,3R,4R)—N2-(4-bromo-2-fluorobenzyl)-N3-(cis-3-fluoropiperidin-4-yl)spiro[bicyclo[2.2.1]heptane-7,1'-cyclopropane]-2,3-dicarboxamide;
(1S,2R,3R,4R)—N2-(4-bromo-2-fluorobenzyl)-N3-(3,3-difluoropiperidin-4-yl)spiro[bicyclo[2.2.1]heptane-7,1'-cyclopropane]-2,3-dicarboxamide;
(1S,2R,3R,4R)—N2-(4-Bromo-2-fluorobenzyl)-N3-(cis-4-fluoropyrrolidin-3-yl)spiro[bicyclo[2.2.1]heptane-7,1'-cyclopropane]-2,3-dicarboxamide; or
(1 S,2R,3R,4R)—N2-(4-Bromo-2-fluorobenzyl)-N3-(trans-4-fluoropyrrolidin-3-yl)spiro[bicyclo[2.2.1]heptane-7,1'-cyclopropane]-2,3-dicarboxamide;
or a salt thereof.

8. The compound according to claim 1, wherein the compound is: (1 S,2R,3R,4R)—N2-(4-bromo-2-fluorobenzyl)-N3-((3S,4S)-3-fluoropiperidin-4-yl)spiro[bicyclo[2.2.1]heptane-7,1'-cyclopropane]-2,3-dicarboxamide; or a salt thereof.

9. The compound according to claim 1, wherein the compound is: (1S,2R,3R,4R)—N2-(4-bromo-2-fluorobenzyl)-N3-((3R,4R)-3-fluoropiperidin-4-yl)spiro[bicyclo[2.2.1]heptane-7,1'-cyclopropane]-2,3-dicarboxamide; or a salt thereof.

10. The compound according to claim 1, wherein the compound is: (1S,2R,3R,4R)—N2-(4-bromo-2-fluorobenzyl)-N3-(cis-3-fluoropiperidin-4-yl)spiro[bicyclo[2.2.1]heptane-7,1'-cyclopropane]-2,3-dicarboxamide; or a salt thereof.

11. The compound according to claim 1, wherein the compound is: (1S,2R,3R,4R)—N2-(4-Bromo-2-fluorobenzyl)-N3-(trans-4-fluoropyrrolidin-3-yl)spiro[bicyclo[2.2.1]heptane-7,1'-cyclopropane]-2,3-dicarboxamide; or a salt thereof.

12. A medicament comprising the compound according to claim 1, or a pharmaceutically acceptable salt thereof.

13. A pharmaceutical composition comprising, as active principle, a compound according to claim 1, or a pharmaceutically acceptable salt thereof, and at least one therapeutically inert excipient.

14. A method of treating a disease comprising administering to a subject in need thereof a compound according to claim 1, wherein the disease is inflammatory diseases, obstructive airway diseases, allergic conditions, HIV-mediated retroviral infections, cardiovascular disorders, neuroinflammation, neurological disorders, pain, prion-mediated diseases or amyloid-mediated disorders.

15. A method of treating a disease comprising administering to a subject in need thereof a pharmaceutical composition according to claim 13, wherein the disease is inflammatory diseases, obstructive airway diseases, allergic conditions, HIV-mediated retroviral infections, cardiovascular disorders, neuroinflammation, neurological disorders, pain, prion-mediated diseases or amyloid-mediated disorders.

16. A method of modulating an immune response comprising administering to a subject in need thereof a compound according to claim 1.

17. A method of modulating an immune response comprising administering to a subject in need thereof a pharmaceutical composition according to claim 13.

* * * * *